United States Patent
Graham et al.

(10) Patent No.: US 6,974,694 B2
(45) Date of Patent: Dec. 13, 2005

(54) ADENOVIRUSES FOR CONTROL OF GENE EXPRESSION

(75) Inventors: Frank L. Graham, Hamilton (CA); Martina Anton, Hamilton (CA); Silvia Bacchetti, Hamilton (CA); Ping Wang, Hamilton (CA); Michael A. Rudnicki, Dundas (CA); William J. Muller, Dundas (CA)

(73) Assignee: AdVec, Inc. (CA)

( * ) Notice: Subject to any disclaimer, the term of this patent is extended or adjusted under 35 U.S.C. 154(b) by 142 days.

(21) Appl. No.: 09/981,685

(22) Filed: Oct. 17, 2001

(65) Prior Publication Data

US 2003/0100523 A1 May 29, 2003

Related U.S. Application Data

(63) Continuation of application No. 09/415,899, filed on Oct. 8, 1999, now abandoned, which is a continuation-in-part of application No. 08/486,549, filed on Jun. 7, 1995, now Pat. No. 6,120,764.

(51) Int. Cl.$^7$ ........................ C12N 15/861; C12N 15/87
(52) U.S. Cl. ..................................... 435/320.1; 435/462
(58) Field of Search ............................. 435/320.1, 462, 435/456; 514/44

(56) References Cited

U.S. PATENT DOCUMENTS

| | | | |
|---|---|---|---|
| 4,510,245 A | | 4/1985 | Cousens et al. |
| 4,797,368 A | | 1/1989 | Carter et al. |
| 4,920,209 A | | 4/1990 | Davis et al. |
| 4,920,211 A | | 4/1990 | Tibetts et al. |
| 4,959,317 A | * | 9/1990 | Sauer .................. 435/172.3 |
| 5,434,066 A | | 7/1995 | Bebee et al. |
| 5,670,488 A | | 9/1997 | Gregory et al. |
| 5,817,492 A | | 10/1998 | Saito et al. |
| 5,882,877 A | | 3/1999 | Gregory et al. |

FOREIGN PATENT DOCUMENTS

| | | |
|---|---|---|
| EP | 0300422 | 1/1989 |
| WO | WO 93/06223 | 4/1993 |
| WO | WO 93/19092 | 9/1993 |
| WO | WO 93/19191 | 9/1993 |
| WO | WO 94/08026 | 4/1994 |
| WO | WO 94/12649 | 6/1994 |
| WO | WO 95/27071 | 10/1995 |
| WO | WO 96/13597 | 4/1996 |
| WO | WO 97/25446 | 7/1997 |
| WO | WO 97/32481 | 9/1997 |

OTHER PUBLICATIONS

Berkner, Current Topics in Microbiology and Immunology, vol. 158, pp. 39–66 (1992).*
Anton et al., J. Virology, vol. 69, No. 8, pp. 4600–46060 (Aug. 1995).*
Kanagae et al., Nucleic Acids Research, vol. 23, No. 19, pp. 3816–3821 (1995).*
Graham, F.L., 1987. Growth of 293 cells in suspension culture. J. Gen. Virol. 68: 937–940.
Quantin, B., Leslie D. Pericaudet, Shahragim Tajbakhsh and Jean–Louis Mandel. 1992 Adenovirus as an expression vector in muscle cells in vivo. Proc. Nt'l. Acad. Sci. 89: 2581–2584.
Bett, A.J., Wael Haddara, Ludvik Prevec and Frank L. Graham. 1994. Proc. Nat'l. Acad Sci. 91: 8802–8806.

(Continued)

Primary Examiner—Terry McKelvey
Assistant Examiner—Nancy T. Vogel
(74) Attorney, Agent, or Firm—Joseph Fischer; Beusse, Brownlee, Wolter, Mora & Maire, PA

(57) ABSTRACT

The invention claims a class of adenovirus vectors for delivering recombinases to a large number of cells of different origins, and methods for regulating the expression of a gene in transfected mammalian cells in culture and in cells of transgenic animals, comprising infecting said cells with an Ad vector encoding a recombinase whose target site is present at or adjacent to the gene, wherein the action of the recombinase regulates the expression of said gene.

15 Claims, 15 Drawing Sheets

CONSTRUCTION OF ADCRE VECTORS

OTHER PUBLICATIONS

Rosenfeld, M.A. et al., 1992. In vivo transfer of the human cystic fibrosis transmembrane conductance regulator gene to the airway epithelium, Cell. 68: 143–155.

W.J. McGrory, D.S. Baulista and F.L. Graham. 1988. A simple techinque for the resue of early region 1 mutations into infectious human adenovirus type 5, Virology 163: 614–617.

Orkin et al., Report and recommendations of the panel to assess the NIH investment in research on gene therapy. Distributed by the National Institutes of Health, Bethesda, MD, Dec. 7, 1995.

Russ, Andreas P., et al. 1996. Self–deleting Retrovirus Vectors for Gene Therapy. J. of Virology, pp. 4927–4932.

Wang, P., Anton, F.L. Grahan, and S. Bacchetti. High Frequency recombination between loxP sites in human chromosomes mediated by an adenovirus vector expressing Cre recombinase. Somatic Cell and Molecular Genetics. vol. 21. 1995, pp 429–441.

Sauer, Brian and Nancy Henderson. 1998. Site–specific DNA recombination in mammalian cells by the Cre recombinase of bacteriophage P1. Proc. Nat'l. Acad. Sci. USA 85: 5166–5170.

Gudrun Schiedner, et al., 1998. Genomic DNA transfer with a high–capacity adenovirus vector results in improved in vivo gene expression and decreased toxicity. Nature Genetics 18: 180–183.

Manal A. Morsy, et al., 1998. An Adenoviral vector deleted for all viral coding sequences results in enhanced safety and extended expression of a leptin transgene. Proc. Nat'l. Acad. Sci. USA 95: 7866–7871.

Parks, et al., 1996. A helper–dependent adenovirus vector system: Removal of helper virus by Cre–mediated excision of the viral packaging signal. Proc. Nat'l. Acad. Sci. USA 93: 13565–13570.

Stephen Hardy, et al., 1997. Construction of Adenovirus Vector through Cre–lox Recombination. Jour. Virol. 71:3 1842–1849.

Metzger, D., J. Clifford, H. Chiba and P. Chambon. 1995. Conditional site–specific recombination in mammalian cells using a ligand–dependent chimeric Cre protein. Proc. Nat'l. Acad. Sci. USA 92: 6991–6995.

Pichel, J.G., Lakso, and Westphal. 1993. Timing of SV40 oncogene activation by site–specific recombination determines subsequent tumor progression during murine lens development. Oncogene 8: 3333–3342.

Sauer, B.. 1994. Site–specific recombination: developments and application. Cur. Opin. Biotech. 5: 521–527.

Sauer, B. and N. Henderson. 1989. Cre–stimulated recombinatin of loxP–containing DNA sequences placed into the mammalian genome. Nucl. Acids Res. 17: 147–161.

Sauer, B., and N. Henderson. 1990. Targeted Insertion of exogenous DNA into the eukaryotic genome by the Cre–recombinase. The New Biologist 2: 441–449.

Sauer, B., M. Whealy, A. Robbins and L. Enquist. 1987. Site–specific insertion of DNA into a pseudorabies virus vector. Proc. Nat'l. Adac. Sci. USA 84: 9108–9112.

Smith A.J., M.A. Desousa, B. Kwabi–Addo, A. Heppell–Parton, H. Impey, and P. Rabbits. 1995. A site–directed chromosomal translocation induced in embryonic stem cells by Cre–loxP recombination. Nature Genetics 9: 376–385.

Rabbits, 1995. A site–directed chromosomal translocation induced in embryonic stem cells by Cre–loxP recombination. Nature Genetics 9: 376–385.

Sternberg, N., B. Sauer, R. Hoess, and K. Abremski. 1986. Bacteriophase P1 cre gene and its regulatory region; Evidence for multiple promotors and for regulation by DNA methylation. J. Mol. Biol. 187: 197–212.

Van Deursen, J. M. Fornerod, B. Van Rees, and G. Grosveld. 1995. Cre–mediated site specific translocation between non–homologous mouse chromosomes. Proc. Nat'l. Acad. Sci. USA 92: 7376–7380.

Mittal, S.K., McDermott, M.R., Johnson, D.C. Prevec, L., and F.L. Graham. 1993. Monitoring foreign gene expression by a human adenovirus–based vector using the firefly luciferase gene as a reporter. Virus Research, 28: 67–90.

Hanke, T., Frank L. Graham, Kenneth L. Rosenthal and David C. Johnson. 1991. Identification of an immunodomiman cytotoxic t–lymphocyte recognition site in glycoprotein B of herpes simplex virus by using recombinant adenovirus vectors and synthetic peptides. 1991. J. of Virology, 65: 1177–1186.

Anton, M., and F.I. Graham, 1995, Site–specific recombination mediated by an adenovirus vector expressing the Cre recombinase protein: a molecular switch for control of gene expression, J. Virol. 69: 4600–4606.

Araki, K., J. Araki, J.I. Miyazaki, and P. Vassali, 1995, Site–specific recombination of a transgene in fertilized eggs by transient expression of Cre recombinase. Proc. Nat'l. Acad. Sci. USA 92: 160–164.

Bett, A.J., I. Prevec, and F.L. Graham, 1993, Packaging capacity and stability of human adenovirus type 5 vectors, J. Virol. 67, 5911–5921.

Bett, AJ., W. Haddara, L. Prevec, and F.L. Graham, 1994, An efficient and flexible system for construction of adenivorus vectors with insertions of deletions in early region 1 and 3, Proc. Nat'l. Acad. Sci USA 91, 8802–8806.

Crystal, R.G., N.G. McElvancy, M.A. Rosenfield, C.S. Chu, A. Mastrangeli, J.G. Hay, S.L. Brody, H.A. Jaffe, N.T. Eissa, and C. Danel. 1994 Administration of an Adenivorus containing the human CFTR cDNA to the respiratory tract of individuals with cystic fibrosis, Nature Genetics 8: 42–51.

Disanto, J.P., W. Mueller, D. Guy–Grand, A. Fischer, and K. Rajewsky, 1995, Lymphoid development in mice with a targeted deletion of the interleukin 2 receptor chain, Proc. Nat'l. Acad. Sci. USA 92: 377–381.

Gage, P.J., B. Sauer, M. Levin and J.C. Glorioso, 1992, A cell–free recombination system for site–specific Integration of multigenic shuttle plasmids into the herpes simplex virus type 1 genome. J. Virol. 66: 5509–5515.

Graham, F.L. and L. Prevec, 1991, Manipulation of adenovirus vectors. In Murray E.J. (ed.), Methods in Molecular Biology, The Humana Press Inc. Clifton NJ vol. 7 (Gene Transfer and Expression Protocols): 109–128.

Graham, F.L. and L. Prevec, 1992, Adenovirus–based expression vectors and recombinant vacines in: Vaccines; New Approaches in Immunological Problems., ed. Ellis R.W. Butterworth–Heinemann, Boston, MA: 363–390.

Graham, F.L., J. Smiley, W.C. Russel, and R. Nairn. 1977. Characteristics of a human cell line transformed by DNA from human adenovirus type 5, J. Gen Virol. 36: 59–72.

Gu, J.H., D. Marth, P.C. Orban, H. Mossmann, and K. Rajewsky, 1994, Deletion of a DNA polymerase B gene segment in T cells using cell type–specific gene targeting. Science 265: 103–106.

Kilby, N.J., M.R. Snaith, and J.A.H. Murray, 1993, Site–specific recombinases; tools for genome engineering. Trends Genet. 9: 413–421.

* cited by examiner

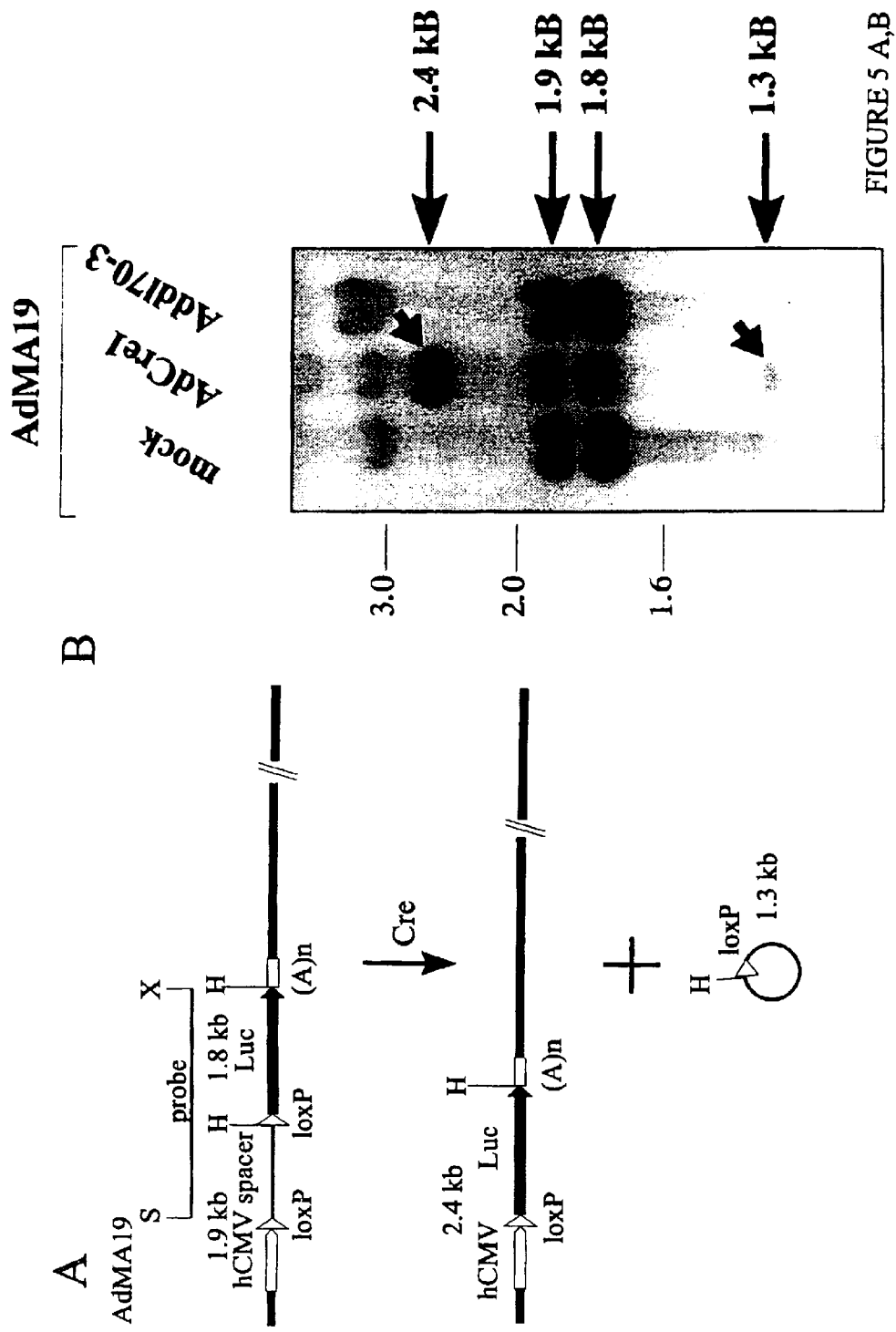
FIGURE 5 A,B

EXPRESSION OF LUCIFERASE IN AD VECTOR INFECTED CELLS

Expt. 1

Expt. 2

STRUCTURE OF INTEGRATED SEQUENCES IN CELL LINE PW27C2

EXPRESSION OF NEO RESULTING IN G418 RESISTANCE

SOUTHERN BLOT HYBRIDIZATION ANALYSIS OF DNA FROM CELL LINES INFECTED WITH ADCRE

IN VIVO GENE EXPRESSION CONTROLLED BY A MOLECULAR SWITCH

TRANSGENICS CONTAINING GENES
CONTROLLED BY A MOLECULAR SWITCH

EXPRESSION OF $\beta$-Gal, Rb, P53, Neu ETC.

SEQUENCE LISTING

<160> NUMBER OF SEQ ID NOS: 3

<210> SEQ ID NO 1
<211> LENGTH: 51
<212> TYPE: DNA
<213> ORGANISM: Artificial Sequence
<220> FEATURE:
<223> OTHER INFORMATION: Plasmid pMA19

<400> SEQUENCE: 1
ggatccaata acttcgtata gcatacatta tacgaagtta taagtactca a    51

<210> SEQ ID NO 2
<211> LENGTH: 15
<212> TYPE: DNA
<213> ORGANISM: Artificial Sequence
<220> FEATURE:
<223> OTHER INFORMATION: Plasmid pMA19

<400> SEQUENCE: 2
aagcttgggc tgcag    15

<210> SEQ ID NO 3
<211> LENGTH: 67
<212> TYPE: DNA
<213> ORGANISM: Artificial Sequence
<220> FEATURE:
<223> OTHER INFORMATION: Plasmid pMA19

<400> SEQUENCE: 3
ataacttcgt atagcataca ttatacgaag ttattaaggg ttccggatcc ccactgaatt    60
cggatcc    67

ADENOVIRUSES FOR CONTROL OF GENE EXPRESSION

CROSS-REFERENCE TO RELATED APPLICATIONS

This application is a continuation of application Ser. No. 09/415,899, filed Oct. 8, 1999, abandoned which is a continuation-in-part of application Ser. No. 08/486,549, filed Jun. 7, 1995, now U.S. Pat. No. 6,120,764. The benefit of priority under 35 USC § 120 is claimed for all of the foregoing applications.

REFERENCE TO SEQUENCE LISTING

A sequence listing is provided separately, both as a CRF on a compact disc, and as a separate paper copy. The Sequence Listing of the CRF is identical to the paper copy Sequence Listing.

FIELD OF THE INVENTION

The present invention relates to adenovirus vectors useful for altering DNA sequences and for controlling gene expression in mammalian cells and in transgenic animals. The vector systems described herein employ a adenovirus vector or vectors that express a recombinase that can excise or rearrange DNA sequences that contain target sites for the recombinase resulting in regulated expression of genes in the vicinity of the target sites. The described system has the ability to switch gene expression on or off in mammalian cells in culture or in transgenic animals. The system also has utility in the isolation of novel cell lines or transgenic animals generated by action of recombinases.

BACKGROUND OF THE INVENTION

The Cre-loxP system of bacteriophage P1 has been shown to efficiently generate recombinant nucleic acids which may encode hybrid proteins. This system requires only two well-characterized components: a 38 kDa recombinase protein, Cre, and a 34 bp loxP target sequence (Kilby, N. J., M. R. Snaith, and J. A. H. Murray. 1993, Trends Genet. 9: 413–421.). Cre binds to the two 13 bp inverted repeats of loxP and catalyzes precise recombination between the asymmetric 8 bp core regions of two loxP sites (Kilby, N. J., M. R. Snaith, and J. A. H. Murray. 1993, Trends Genet. 9: 413–421.). Recombination between two parallel sites, as defined by the core region, results in excision of intervening sequences producing two recombination products each containing one loxP site, whereas recombination between antiparallel sites inverts the bracketed fragment. Intermolecular recombination between loxP sites on separate plasmids results in integration of sequences bracketed by loxP sites. The Cre-loxP system has been shown to function in both bacteria (Sternberg, N., B. Sauer, R. Hoess, and K. Abremski. 1986, J. Mol. Biol. 187: 197–212.) and eukaryotic cells (Sauer, B., and N. Henderson. 1989, Nucl. Acids Res. 17: 147–161.) and has been exploited for the excision (Sauer, B., and N. Henderson. 1989, Nucl. Acids Res. 17: 147–161.) and the integration of fragments in cellular and viral genomes (Sauer, B., and N. Henderson. 1990, The New Biologist 2: 441–449.; Sauer, B., M. Whealy, A. Robbins, and L. Enquist. 1987, Proc. Natl. Acad. Sci. USA 84: 9108–9112.). The use of Cre in cell-free systems for construction of recombinant vectors has also been reported (Gage, P. J., B. Sauer, M. Levine, and J. C. Glorioso. 1992, J. Virol. 66: 5509–5515; Sauer, B., M. Whealy, A. Robbins, and L. Enquist. 1987, Proc. Natl. Acad. Sci. USA 84: 9108–9112.).

Cre-loxP based recombination has further been used successfully for tissue-specific gene expression or deletion in transgenic mice (Pichel, J. G., M. Lakso, and H. Westphal. 1993, Oncogene 8: 3333–3342.; Gu, H., J. D. Marth, P. C. Orban, H. Mossmann, and K. Rajewsky. 1994, Science 265: 103–106.). In the latter cases, the recombinase was delivered by transfection (Gu, H., J. D. Marth, P. C. Orban, H. Mossmann, and K. Rajewsky. 1994, Science 265: 103–106.) or micro injection (Araki, K., M. Araki, J.-I. Miyazaki, and P. Vassalli. 1995, Proc. Natl. Acad. Sci. USA 92: 160–164.; Pichel, J. G., M. Lakso, and H. Westphal. 1993, Oncogene 8: 3333–3342.) of Cre encoding plasmids into ES cells or fertilized eggs.

SUMMARY OF THE INVENTION

It is an object of the invention to develop new approaches and vectors for the efficient generation of recombinant nucleic acids and for the expression of these recombinant nucleic acids in a wide variety of organisms, tissues, and cells in cell culture. It is particularly an object to providing a means for delivery of the Cre recombinase protein to a large number of cells of different origins, and for using the Cre to effect recombination events in the transformed cells. It is also particularly an object of the invention to develop adenovirus vectors that express recombinase enzymes or other DNA modifying enzymes that alter DNA structure. It is specifically an object to develop such vectors using the recombinant plasmids, viral vectors, and techniques disclosed in the parent applications to this application.

Accordingly, this invention teaches the construction and use of Ad vectors in which the Cre protein is expressed under control of the human cytomegalovirus (HCMV) immediate early gene promoter.

We also demonstrate that the system can be used to induce expression of a reporter gene by coinfection of cells with two Ad vectors, one carrying the luciferase gene under the control of a "molecular switch" that can be turned on by the second vector expressing Cre. We further show that delivery of the Ad vector carrying the Cre recombinase gene to mammalian cells that have the Cre target sequence (loxP) integrated into their chromosomal DNA can induce rearrangement of the DNA as a result of the activity of the Cre enzyme and its ability to induce recombination between two or more loxP sites. Depending on the structure of DNA sequences flanked by or adjacent to the loxP sites, excision or rearrangement of DNA sequences flanked by loxP can, as a result of the action of the Cre recombinase, result in expression of an adjacent gene that is otherwise dormant or can result in shut-off of gene expression if genes are engineered to be active until DNA sequences within or in the vicinity of an otherwise active gene are acted upon by the recombinase.

BRIEF DESCRIPTION OF FIGURES

FIG. 5A is a diagrammatic representation of the structure of an Ad vector containing a reporter gene (luc) separated from a promoter by a spacer DNA flanked by loxP sites, and the effect of Cre activity on the DNA structure of the vector.

FIG. 5B illustrates the ability of Cre synthesized in cells infected by AdCre to catalyze excision of a DNA segment flanked by loxP sites from AdMA19 in an in vivo reaction in cells coinfected with AdCre and AdMA19.

DETAILED DESCRIPTION OF THE INVENTION

Overview of the Invention

Figure 1:
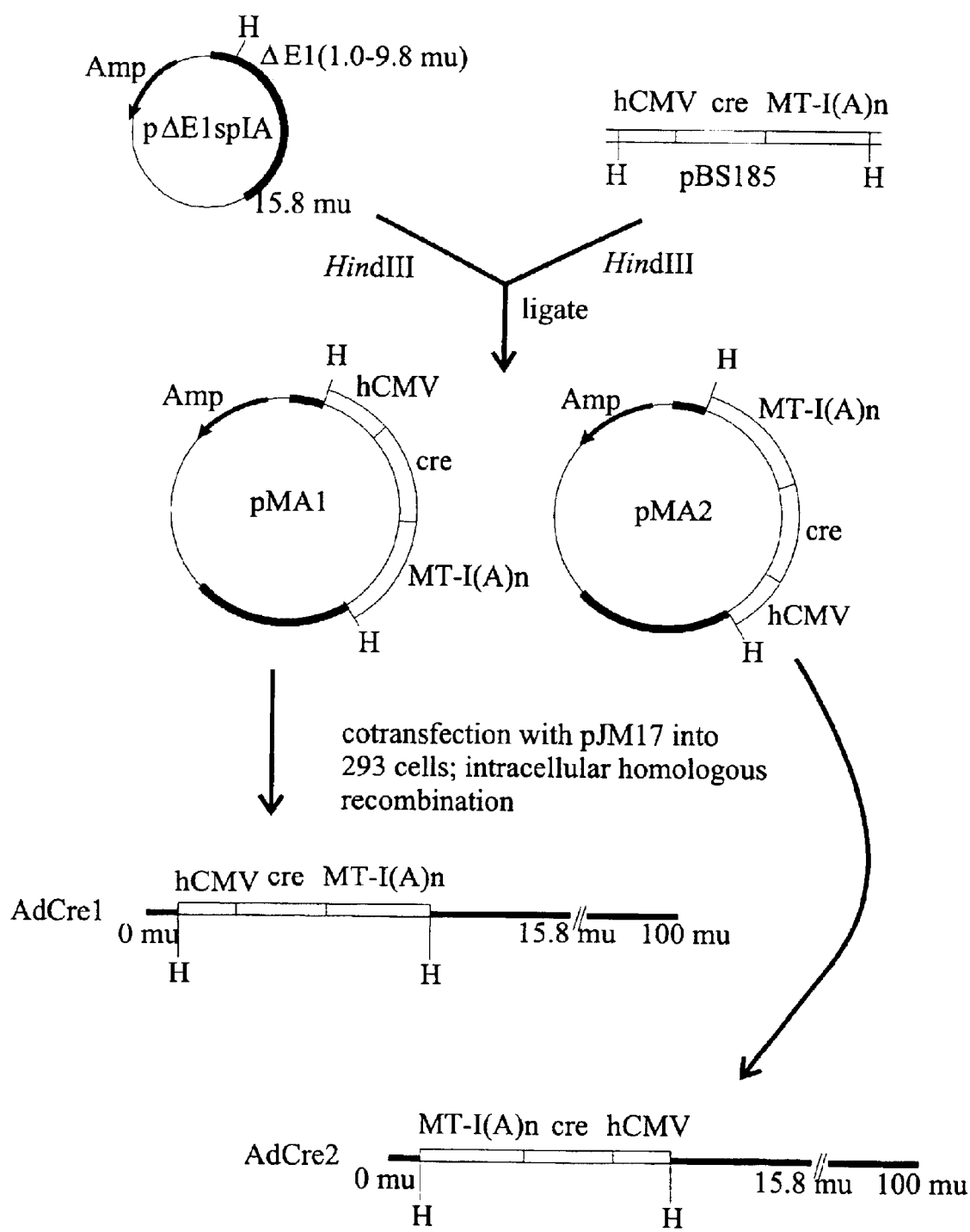
FIG. 1 is a diagrammatic representation of the structure and construction of Cre expressing plasmids and viruses.

Application Ser. No. 08/250,885, filed on May 31, 1994, disclosed a defined genus of human adenovirus (Ad) vectors useful for heterologous gene expression in mammalian cells. These Ad vectors have a number of properties that render them particularly suited for the applications that are described below. The 36 kbp double stranded DNA genome is relatively easy to manipulate with recombinant DNA techniques, helper independent vectors can accommodate up to 8 kbp of foreign DNA depending on the system chosen, and Ad virions are physically and genetically stable if the vectors are constructed and propagated appropriately. Viruses with a deletion in E1 can be propagated on 293 cells, and can infect but not replicate in other human cell lines. Ad5 can be grown to high titers and can infect a wide variety of tissues, such as epithelial and endothelial cells, fibroblasts, stromal cells, and hepatocytes of different species. Moreover Ad can infect quiescent as well as replicating cells and express proteins therein. Adenovirus vectors have the capability of delivering genes to tissues in many different animals and of inducing expression of proteins encoded by such vectors in vivo. Thus adenovirus vectors expressing a recombinase such as Cre afford the possibility of delivering and producing the Cre enzyme, or an analogous recombinase such as the FLP recombinase of yeast, to a wide variety of mammalian cell types or to a wide variety of tissues in animals.

As established in the parent applications, adenoviruses (Ads) have several properties that make them attractive for gene transfer and gene therapy. They can be grown to high titers and can infect a variety of cell types from a variety of species and can be injected into tissues of animals of various species and will express a foreign gene product cloned in the Ad genome. Transduced genes can be expressed in both dividing and non dividing cells of many tissues. Deletion of Ad early region 1 (E1) can be combined with a deletion of early region 3 (E3) and together these deletions provide for a packaging capacity for insertion of foreign DNA of up to 8000 bp into either the E1 or E3 region of an Ad vector. Alternatively, either E1 or E3 may be left intact. If E1 is left intact, a foreign DNA may be introduced into the E3 region and the resulting Ad vector may replicate in any normally permissive cell. If E1 is removed from the viral genome, the resulting vector is defective for replication in most cells but may be propagated in human 293 cells. Such a vector is said to be attenuated and will fail to replicate in cells other than 293 cells but can nonetheless infect human and non human mammalian cells and deliver foreign DNA into such cells. Appropriately designed and engineered foreign genes introduced into cells by Ad vectors will express proteins encoded by such genes. E1 deleted vectors can persist and continue to express the products of cloned foreign genes in infected cells in culture or in cells of animals injected with the vector for extended periods. Thus a vector designed and engineered to express a recombinase or other DNA modifying enzyme will express the enzyme in infected cells either in vitro or in vivo and act on target DNA sites to induce rearrangements, deletions, or inversions of DNA segments that contain the target DNA of the recombinase. This can have the effect of turning on, or off, expression of an appropriately designed and engineered gene present in the cells. Since the virus does not integrate efficiently, expression of the recombinase should be transient so that once a molecular switch has been turned on or off by the action of a recombinase expressed from a vector, the switch should remain on, or off, respectively.

We therefore explored the possibility of introducing into an Ad5 vector, coding sequences for a particular recombinase, that known as "Cre" from P1 bacteriophage which acts on a specific 34 base pair DNA sequence known as "loxP" and will catalyze rearrangement of DNA sequences that contain loxP. The Cre coding DNA sequences were introduced into the E1 region of an Ad5 vector from which E1 sequences had been removed using plasmids and techniques described in the parent applications and in FIG. 1. The Cre coding sequences were flanked by a promoter element (HCMV IE gene promoter) derived from the human cytomegalovirus genome and a polyadenylation signal derived from SV40 (simian virus 40) DNA. Similar vectors containing Cre encoding sequences flanked by other transcriptional regulatory sequences can also be employed. Furthermore, the insertion site for the Cre gene need not be limited to the E1 region of the viral genome but could equally be placed in early region 3 or in such other regions of the viral genome as might be suitable and as might allow the vector to replicate in suitable cells. Furthermore, Ad vectors based on other adenoviruses of either human origin or isolated from other animals would be equally suitable.

Throughout this application various publications are referenced within parentheses. The disclosures of these publications in their entireties are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise. Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting of the invention. For example, the term "gene" includes cDNAs, RNA, or other polynucleotides that encode gene products. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives can be made and will hybridize to one another and to DNA and RNA, and the use of such analogues and derivatives is also within the scope of the present invention.

"Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers primarily to proteins and polypeptides encoded by a nucleic acid, but further encompasses nucleic acids encoded by other nucleic acids (e.g., non-coding and regulatory RNAs such as tRNA, sNRPs). The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, Genomics 4: 560–569 (1989); Landren et al., Science 241: 1077–1080 (1988); Nickerson et al., Proc. Natl. Acad. Sci. 87: 8923–8927 (1990); Barany, F., Proc. Natl. Acad. Sci. 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., PCR Methods and Applications 1: 5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats. The detection oligonucleotide probes range in size between 10–1,000 bases. In order to obtain the required target discrimination using the detection oligonucleotide probes, the hybridization reactions are generally run between 20–60.degree. C., and most preferably between 30–50.degree. C. As known to those skilled in the art, optimal discrimination between perfect and mismatched duplexes is obtained by manipulating the temperature and/or salt concentrations or inclusion of formamide in the stringency washes.

The cloning and expression vectors described herein are introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by references, and in Ausubel et al., Current Protocols in Molecular Biology, John Wiley and Sons, Baltimore, Md. (1989), which is also hereby incorporated by reference. The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody secreting hybridoma cells. The bank of hybridomas is screened for clones that secrete immunoglobulins which bind the recombinantly produced fragment. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic oligonucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and, optionally, sequences necessary for replication of a vector. *E. coli* is one prokaryotic host useful particularly for cloning DNA sequences of the present invention. Other microbial hosts suitable for use include bacilli, such as *Bacillus subtilis,* and other Enterobacteriaceae, such as *Salmonella, Serratia,* and various *Pseudomonas* species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation. Other microbes, such as yeast, are used for expression. Saccharomyces is a suitable host, with suitable vectors having expression control sequences, such as promoters, including 3-phosphoglycerate kinase or other glycolytic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

The method lends itself readily to the formulation of test kits for use in diagnosis. Such a kit comprises a carrier compartmentalized to receive in close confinement one or more containers wherein a first container contains suitably labeled DNA probes. Other containers contain reagents useful in the localization of the labeled probes, such as enzyme substrates. Still other containers contain restriction enzymes, buffers etc., together with instructions for use.

EXAMPLE 1

Construction of Cre Expressing Plasmids and Viruses.

Figure 4:
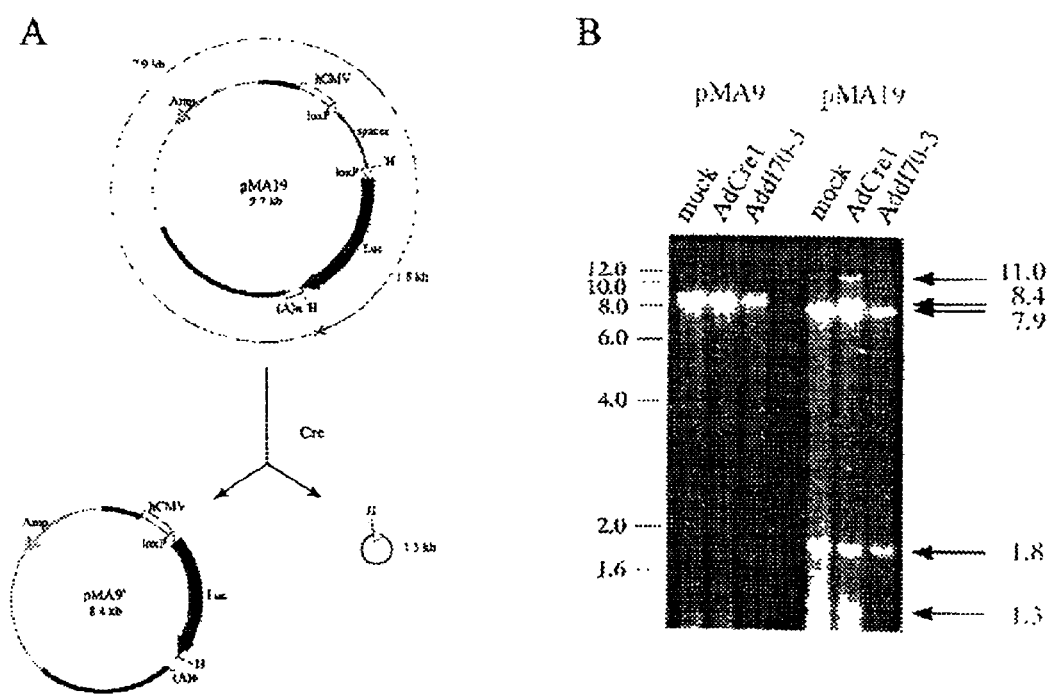
FIG. 4A is a diagrammatic representation of the DNA rearrangements induced by Cre in an In vitro recombination assay with pMA9 and pMA19.
FIG. 4B illustrates the ability of Cre synthesized in cells infected by AdCre to catalyze excision of a DNA segment flanked by loxP sites from pMA19 in an in vitro reaction.

Plasmids pMA1 and pMA2 were constructed by inserting the HindIII fragment of pBS 185 containing the Cre orf under control of the HCMV immediate early promoter and the metallothionein-I poly-adenylation signal into the unique HindIII site of p.DELTA.E1spIA (described in FIG. 4 of parent application). AdCre1 and AdCre2 were derived by cotransfection of pJM17 (McGrory, J., D. Bautista, and F. L. Graham. 1988, Virol. 163: 614–617) and pMA1 and pMA2, respectively, into 293 cells. FIG. 1 Thin lines represent plasmid sequences, solid bars Ad sequences. The Cre orf, HCMV promoter and the metallothionein-I polyadenylation signal (MT-I(A)n) are indicated. H: HindIII. Plasmid sizes and the left end of the viruses are drawn approximately to scale.

EXAMPLE 2

Detection of Cre Expression in AdCre Infected Human Cells.

Figure 2:
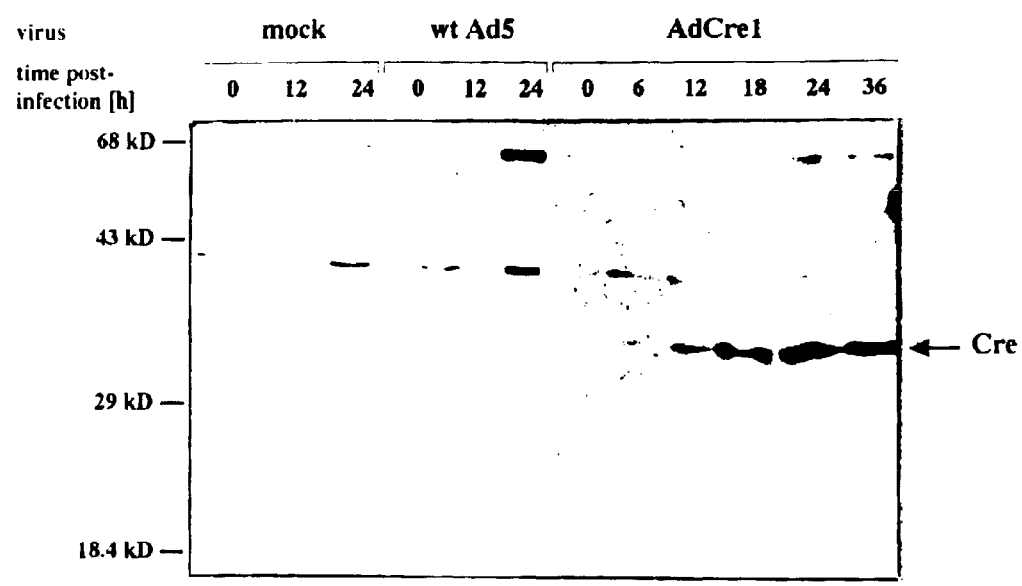
FIG. 2 illustrates detection of Cre expression in 293 cells by Western blot analysis with antibody specific for Cre protein.

Production of the Cre protein by AdCre infected cells was analyzed by Western blot, using a Cre-specific polyclonal antibody (Sauer, B. 1987, Mol. Cell. Biol. 7: 2087–2096). In initial experiments, 293 cells were infected with AdCre1 or wt Ad5 at an m.o.i. of 20 or were mock infected, and harvested at various times post-infection. Infected cell extracts were made and proteins were separated on a 10% SDS polyacrylamide gel, transferred to an Immobilon membrane, and detected by Cre specific antibodies. FIG. 2. Molecular weights are given on the left, the arrow on the right indicates the position of the 38 kD Cre protein. Expression of the 38 kDa Cre protein was detectable as early as 6 hours after infection with AdCre1, and increased up to 24 hours. No further increase was seen at later times (e.g. 36 hours), presumably due to the onset of cell lysis since 293 cells are permissive for replication of the E1-deficient AdCre1 vector. Cells infected with wt Ad5 or mock-infected did not express the Cre protein, but contained several proteins which appeared to be nonspecifically stained by the polyclonal serum and which were also detected in AdCre1 infected samples. The 60 kDa species, detected only in infected cells, is likely to correspond to the virus fibre protein which is produced at high levels late in infection.

Expression of Cre protein was also detectable between 24 h and 96 h post-infection in AdCre1 infected MRC5 cells (m.o.i. of 50), but not in infections with the E1 deletion virus Add170-3 (Bett, A. J., W. Haddara, L. Prevec, and F. L. Graham. 1994, Proc. Natl. Acad. Sci. USA 91: 8802–8806) at the same m.o.i. or in uninfected MRC5 cells (data not shown). Thus high levels of Cre protein are produced in infected human 293 or MRC5 cells.

Since levels of Cre expression obtained with AdCre1 or AdCre2 did not differ substantially (data not shown), AdCre1 was chosen for further experiments.

EXAMPLE 3

Construction of Regulated Reporter Plasmids and Viruses.

To obtain a protein expression system that could be regulated by Cre-catalyzed recombination we designed an expression cassette in which the luciferase cDNA (Luc) and the HCMV promoter were separated by a spacer region flanked by loxP sites that would prevent luciferase expression unless the spacer was excised. As the recombination product would still contain one loxP site between regulatory and coding sequences it could not be predicted that luciferase could be expressed following excision of the spacer by Cre mediated recombination. We initially investigated whether insertion of loxP in this position would allow expression of luciferase. Isolation of such a vector would confirm that Ad5 could tolerate the palindromic loxP sequence in addition to the terminal inverted repeats.

Figure 3A:
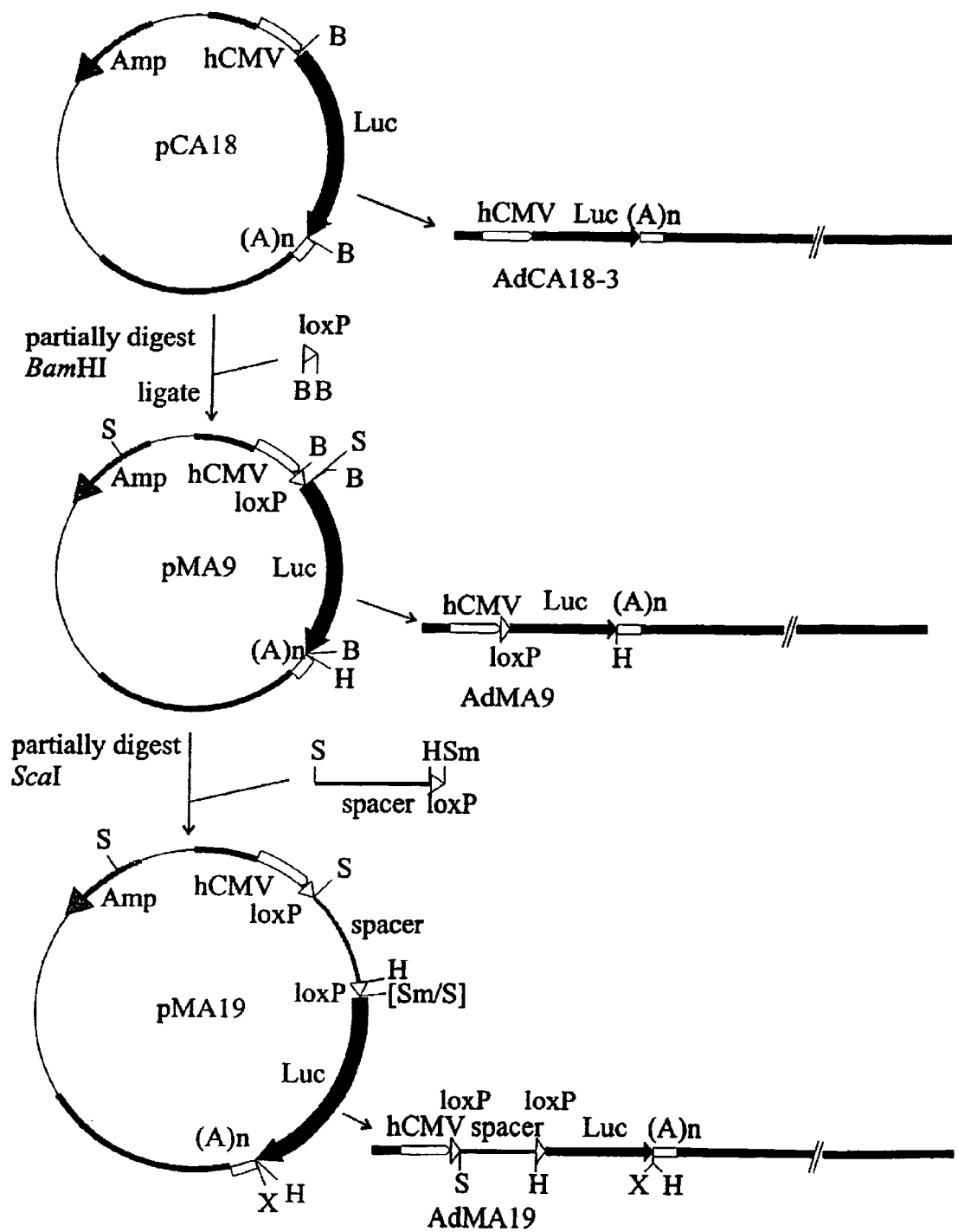
FIGS. 3A and 3B are a diagrammatic representation of the structure and construction of regulated reporter plasmids and viruses that can express firefly luciferase following excision of DNA by action of Cre recombinase, and depicts SEQ ID NO:1, SEQ ID NQ:2, and SEQ ID NO:3.

Plasmid constructions started with pCA18 which has the E1 region substituted with the HCMV immediate early promoter and the firefly luciferase gene, Luc (9), in the left to right orientation (pCA 18 was derived from pCA14 (FIG. 1 of application Ser. No. 08/262,091, filed Jun. 20, 1994 now abandoned: "Direct intratumoural injection of Recombinant Adenovirus Vectors and Viral Particles that Encode Cytokines, to Obtain Shrinkage and Elimination of Tumors") by insertion of the Luc cDNA into the BamHI cloning site of pCA14 to place the Luc cDNA under control of the HCMV immediate early promoter. (A)n designates the SV40 poly-adenylation signal.). A synthetic loxP site flanked by BamHI compatible ends was inserted into the unique BamHI site between the HCMV promoter and the luciferase cDNA in such a way that no translational start codon was introduced in any reading frame upstream of the luciferase ATG (FIG. 3A). (If inserted in the opposite orientation the loxP site adds ATGs in two reading frames.)

The structure of the resulting plasmid, pMA9, was confirmed by digestion with EcoRI and ScaI, and by sequencing of the insert using a primer binding in the 3' region of the HCMV promoter. pMA9 was used with pBHG10 (described in parent application Ser. No. 08/250,885) in cotransfection of 293 cells to obtain AdMA9 (FIG. 3A). Our ability to rescue this virus, and its normal growth properties (data not shown), demonstrate that a loxP site does not interfere with viral DNA replication.

To generate a construct in which the HCMV promoter is separated from the luciferase orf by a spacer region, we chose an unrelated sequence with translational start and stop codons in all reading frames that should block luciferase expression. We inserted the 1.3 kbp ScaI-SmaI fragment of pBS64 (Sauer, B., M. Whealy, A. Robbins, and L. Enquist. 1987, Proc. Natl. Acad. Sci. USA 84: 9108–9112) into pMA9 that had been linearized by SmaI digestion and partially digested by ScaI (FIG. 3A). The resulting plasmid, pMA19, contains two loxP sites in parallel orientation separated by pBS64 sequences which comprise sequences from pUC12, pBR322 and the SP6 promoter (FIG. 3B).

pMA19 was used with pBHG10 to cotransfect 293 cells and obtain the vector AdMA19 (FIG. 3A). AdCA18-3 was obtained by cotransfection of 293 cells with pCA18 and pJM17 (C. Addison, pers. comm.). AdMA9, AdMA19, and AdCA18-3 were further plaque purified before viral stocks were prepared as described previously (Hitt, M., A. Bett, C. Addison, L. Prevec, and F. L. Graham. In K. W. Adolph (ed.), Techniques for Human Adenovirus vectors Construction and Characterization. Methods in Molecular Genetics. Acad. Press, Orlando, Fla. In press). In the diagram in FIG. 3A thin lines represent plasmid sequences, solid bars Ad sequences. The left ends of the resulting Ad vectors are shown in detail. B: BamHI, H: HindIII, S: ScaI, Sm: SmaI, X: XhoI. Plasmid sizes are not drawn to scale.

Figure 3B:
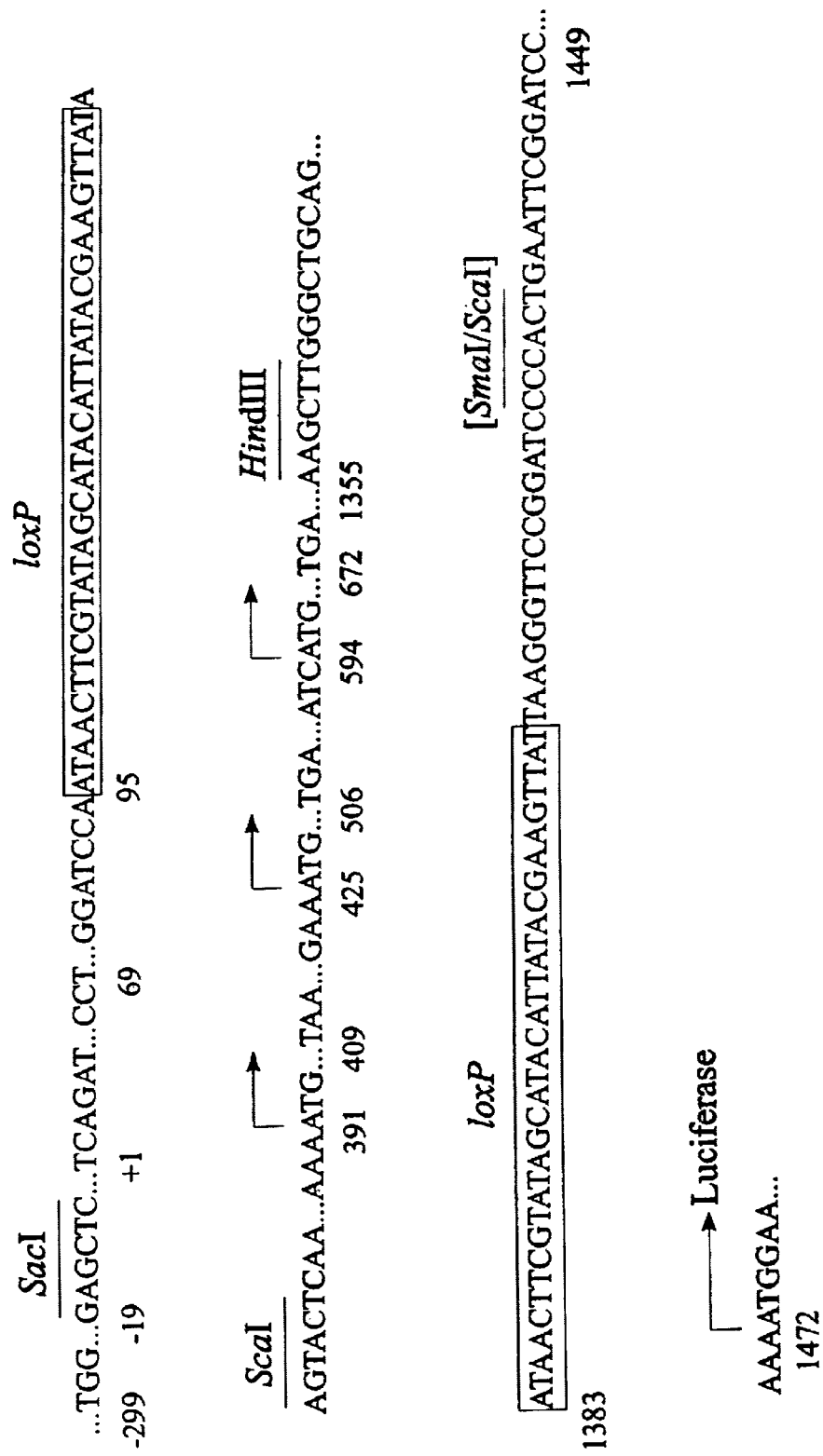

The diagram in FIG. 3b provides details of the loxP flanked spacer sequence inserted between promoter and luciferase cDNA in pMA19 and AdMA19. Numbering begins at the transcription start (+1) from the HCMV promoter (Fickenscher, H., T. Stamminger, R. Rueger, and B. Fleckenstein. 1989, J. Gen. Virol. 70: 107–123). Arrows indicate the luciferase translation start and possible translation starts in all reading frames in the spacer derived from pBS64 and. Only the first ATG in each reading frame preceded by a purine at the −3 position and the corresponding stop codon in the same frame are shown. Relevant restriction sites are given. loxP sequences are boxed.

EXAMPLE 4

Demonstration that Cre was Enzymatically Active.

It could not be predicted that Cre recombinase produced in AdCre infected cells would be enzymatically active. Therefore the biochemical activity of the adenovirus-encoded Cre protein was first determined in a cell free assay: uninfected 293 cells or 293 cells infected with AdCre1 or Add170-3 at an m.o.i. of 10, were harvested 18 h post-infection and cell extracts were prepared by sonication. 50 $\mu$l aliquots were incubated with assay buffer and 1 $\mu$g of pMA9 or pMA19 at 37° C. for 30 minutes. After phenol and chloroform extractions, samples were digested with HindIII and analyzed on an 0.8% agarose gel. HindIII digestion of pMA19 DNA that had been incubated with extracts from mock or Add170-3 infected cells generated a 7.9 kbp and a 1.8 kbp band (FIGS. 4A and 4B). In contrast, when pMA19 was first incubated with extracts from AdCre1 infected 293 cells, HindIII digestion resulted in two novel bands of 8.4 kbp and 1.3 kbp (FIG. 4B). These correspond to the sizes expected for the linearized forms of the two circular products of recombination: pMA9' (identical to pMA9 except for 18 bp due to the cloning procedure) and a second miniplasmid corresponding to the excised spacer (FIG. 4A). HindIII digestion of the control plasmid pMA9 yielded a single linear fragment of 8.4 kbp, irrespective of the extract used for incubation (FIG. 4B), since pMA9 only contains one loxP site which does not allow intramolecular recombination.

We estimated the Cre specific efficiency of recombination to be approximately 50%, as judged by the relative intensities of the bands in FIG. 4B. The fragment of ~11 kbp present only in the Cre-treated sample of pMA19 may represent a Holliday structure ($\chi$) formed as an intermediate of recombination. $\chi$ and $\alpha$ structures, derived from Cre mutants, have been observed previously (Hoess, R., A. Wierzbicki, and K. Abremski. 1987, Proc. Natl. Acad. Sci. USA 84: 6840–6844) as bands migrating with reduced electrophoretic mobility relative to the unrecombined, digested form of the plasmid. It is possible that sonication or storage of the extract may have functionally altered the Cre enzyme, but production of a protein with altered activity in AdCre1 infected cells cannot be ruled out. Thus the Cre recombinase produced in AdCre infected cells was capable of excising a DNA segment flanked by loxP sites in an in vitro recombination assay.

EXAMPLE 5
Demonstration that Cre Induced Recombination.

It was important to determine whether the Cre recombinase produced in infected cells was capable of inducing rearrangement in vivo of DNA sequences flanked by loxP sites. Therefore a simple and sensitive assay was developed that depended on expression of a reporter gene, firefly luciferase, from a promoter that was separated by a DNA segment (spacer) flanked by loxP sites and constructed such that the intervening spacer prevented the expression of the adjacent luciferase gene. Removal of the spacer by intermolecular recombination catalyzed by Cre would allow for expression of luciferase which can be easily detected by a simple enzymatic assay. The expression of firefly luciferase from the recombinant Ad vectors AdCA18-3, AdMA9 and AdMA19 was measured biochemically by emission of light as described previously (Mittal, S. K., M. R. McDermott, D. C. Johnson, L. Prevec, and F. L. Graham. 1993, Virus Res. 28: 67–90).

Figure 5C:
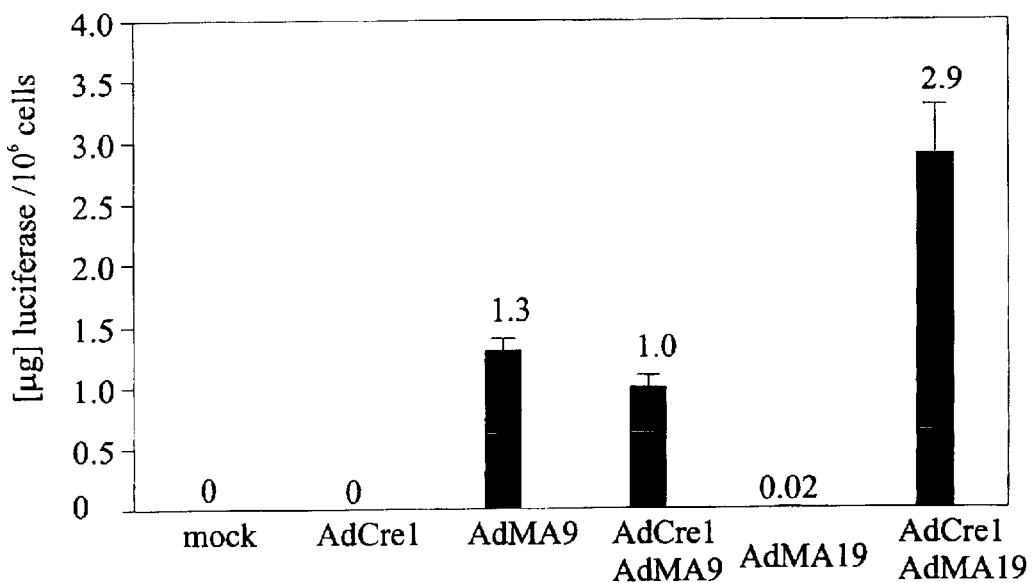
FIG. 5C illustrates the ability of Cre to switch on expression of luciferase in cells coinfected with AdCre and AdMA19.
Figure 5C:
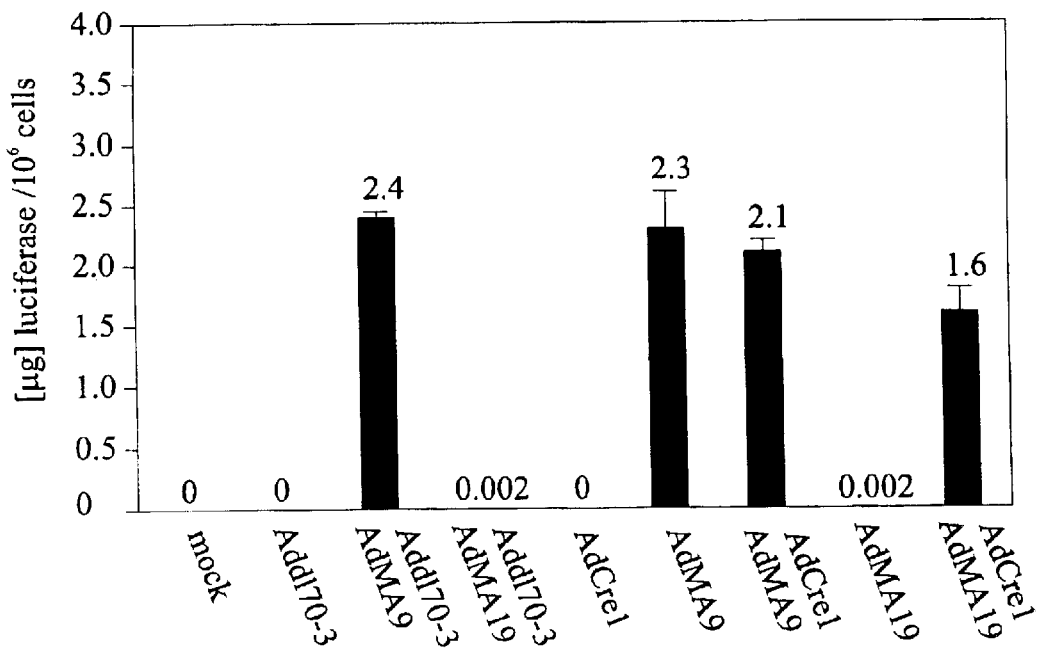

It was important to test the effect of Cre expression in cells that had been infected with an Ad vector that contained the luciferase reporter gene under the control of a promoter that had no intervening spacer segment but had either one or no loxP sites between the promoter and the luciferase cDNA. Infection of 293 cells with AdCA18-3 (no loxP) or AdMA9 (one loxP) at an m.o.i. of 5 and preparation of cell extracts 24 h post infection resulted in a luciferase activity of $0.84+/-0.14$ μg/10.sup.6 cells (AdCA18-3) or $0.61+/-0.03$ μg/10.sup.6 cells (AdMA9), demonstrating that a single loxP site inserted between the HCMV promoter and the translation start for Luc did not significantly alter expression of the gene. In a separate experiment, when 293 cells were infected with AdMA9 at an m.o.i. of 10, a luciferase activity of about 1.3 μg/$10^6$ cells was detected after 24 h (FIG. 5C, expt. 1). In contrast only a low level of activity (20 ng/$10^6$ cells) was obtained from AdMA19 infected cells, indicating that expression of luciferase from this virus was effectively suppressed by the spacer DNA interposed between the promoter and ATG of the reporter gene. To assess the ability of Cre protein produced from AdCre1 to act on loxP-containing Ad vectors, 293 cells were doubly infected with AdCre1 and AdMA9 or AdCre1 and AdMA19 at various multiplicities of infection, and harvested after 24 h. AdCre1 had no significant effect on the activity of luciferase expressed from AdMA9 (FIG. 5C, expt. 1). However, upon double infection with AdCre1 and AdMA19, luciferase was switched on and, depending upon the m.o.i., levels of activity up to 2.9 μg/$10^6$ cells were obtained (FIG. 5C, expt. 1). Induction of luciferase activity suggested that the loxP-flanked spacer, between the HCMV promoter and the luciferase, had been excised. Cre specific recombination, measured as induction of luciferase expression, was also detected in double infections of the non-permissive cell line MRC5 (FIG. 5C, expt. 2). No luciferase activity was observed in cells infected with AdCre1 or Add170-3 or when cells were mock-infected. As was the case with 293 cells, expression of Cre did not alter the luciferase activity produced by infection with AdMA9, but mixed infections with AdMA19 and AdCre1 increased luciferase expression from a background activity of 2 ng/$10^6$ cells up to 1.6 μg/10.sup.6 cells. Double infections with Add170-3 and AdMA19, which did not result in increased luciferase activity, confirmed that the induction was dependent upon the recombining activity of Cre expressed from AdCre1. Although MRC5 cells were infected at higher m.o.i. than 293 cells and harvested after longer times, they expressed lower luciferase activity than infected 293 cells, even at the highest m.o.i. tested. This was consistent with the results of Western blots which indicated that Cre was produced at lower amounts in MRC5 compared to 293 cells (data not shown). The background activity of luciferase observed after infection of 293 or MRC5 cells with AdMA19 alone could be due to spontaneous homologous recombination between the loxP sites resulting in excision of the spacer in a small fraction of viruses. To examine this possibility we performed PCR analyses that would allow detection of recombined viruses.

Amplification of parental AdMA19 DNA using primers binding to the HCMV promoter and the Luc cDNA should result in a fragment of ~1.5 kbp, whereas amplification of AdMA19 viral DNA, from which the 1.3 kbp spacer had been excised by spontaneous or Cre-mediated recombination, should yield a 182 bp fragment derived from the excised spacer. In addition to the 1.5 kbp fragment a faint band of ~180 bp was detected after amplification of AdMA19 viral DNA (data not shown), in support of our hypothesis that spontaneous excision may have occurred in a small sub-population of AdMA19 virions.

Direct demonstration that induction of luciferase activity in cells coinfected with AdMA19 and AdCre1 was due to Cre specific excision of the 1.3 kbp loxP-flanked spacer in AdMA19, was obtained by Southern blot analysis. Viral DNA was extracted 24 h after double infection of 293 cells with AdMA19 and AdCre1 (both at a m.o.i. of 5), and digested with HindIII. Southern hybridization was carried out using as probe the 2.9 kbp ScaI-XhoI fragment of pMA19 containing the firefly luciferase cDNA and the spacer segment derived from pBS64 (FIG. 3A). Unrecombined AdMA19 is represented by the 1.9 and 1.8 kbp bands (from the left end of the virus) obtained after double infection of cells with AdMA19 and Add170-3 or after mock infection (FIGS. 5A and 5B). Upon coinfection with AdCre1, the virus encoded enzyme should mediate recombination resulting in excision of a 1.3 kbp circle from the viral genome (indicated in FIG. 5A as a 1.3 kbp miniplasmid), leaving behind a 2.4 kbp HindIII fragment. All of the predicted fragments were detected by Southern hybridization (FIG. 5B).

From visual comparison of the intensity of the 2.4 kbp band relative to the 1.8 or 1.9 kbp fragments, we estimate that approximately 50% of the AdMA19 viral DNA had undergone recombination under the experimental conditions used (FIG. 5B). Under representation of the 1.3 kbp fragment is due to the fact that the excised miniplasmid does not replicate, in contrast to the viral vector.

Thus, the relative intensity of this band does not reflect the efficiency of the recombination process. The faint bands of 3.1 and 3.4 kbp represent viral DNA fragments, and are detected because of contamination of the probe with viral DNA sequences from pMA19 from which the probe was derived. Since no unexpected fragments were generated in this in vivo assay, we assume that the Cre protein is produced correctly in AdCre1 infected cells, and that the presence of the 11 kbp band, seen in the in vitro assay (FIG. 4B), was likely due to functional alteration of the Cre enzyme for technical reasons.

The results of assays of DNA structural alterations and expression of luciferase indicate that Cre protein produced by AdCre in AdCre infected cells is able to induce specific recombination of sequences in AdMA19 in vivo. The expected recombination products derived from AdMA19 upon coinfection with AdCre1 are shown in FIG. 5A. Solid bars represent viral sequences and loxP sites are shown as open arrow heads. The spacer sequence, blocking luciferase expression is shown as the stippled bar in AdMA19 and as the stippled circle generated by recombination. H: HindIII restriction sites and approximate sizes of the HindIII fragments of the left end of AdMA19, the recombined virus and the excised circle are indicated. The experimental results of analysis of DNA from cells coinfected with AdCre and AdMA19 are shown in FIG. 5B. Viral DNA extracted from 293 cells doubly infected as indicated at the top of the figure was digested with HindIII. The Southern blot of separated DNA was probed with the 2.9 kb ScaI-XhoI fragment of pMA19 (see also FIG. 3A). Molecular weights of marker DNA fragments are given on the left margin and the sizes of fragments derived from unrecombined and recombined viral DNA are indicated on the right. Arrowheads represent the recombination products of AdMA19, as predicted from recombination events shown in A. Only relevant restriction sites are shown. The appearance of DNA fragments at 2.4 kb and 1.3 kb provides evidence for efficient recombination of loxP containing sequences of AdMA19 by action of Cre protein produced by AdCre. Thus AdCre is able to induce expression of functional Cre protein which is able to turn on expression of a reporter gene (luc) controlled by a promoter and spacer sequence in which the spacer is flanked by loxP sites.

EXAMPLE 6

The preceding examples confirm that Cre expressed from AdCre is enzymatically active, both in cell free enzymatic reactions and within infected cells. In particular, the examples described above indicated that Cre produced by the AdCre vector could catalyze recombination and induce rearrangement of DNA sequences containing loxP sites in the genome of a second coinfecting vector.

Figure 6A:
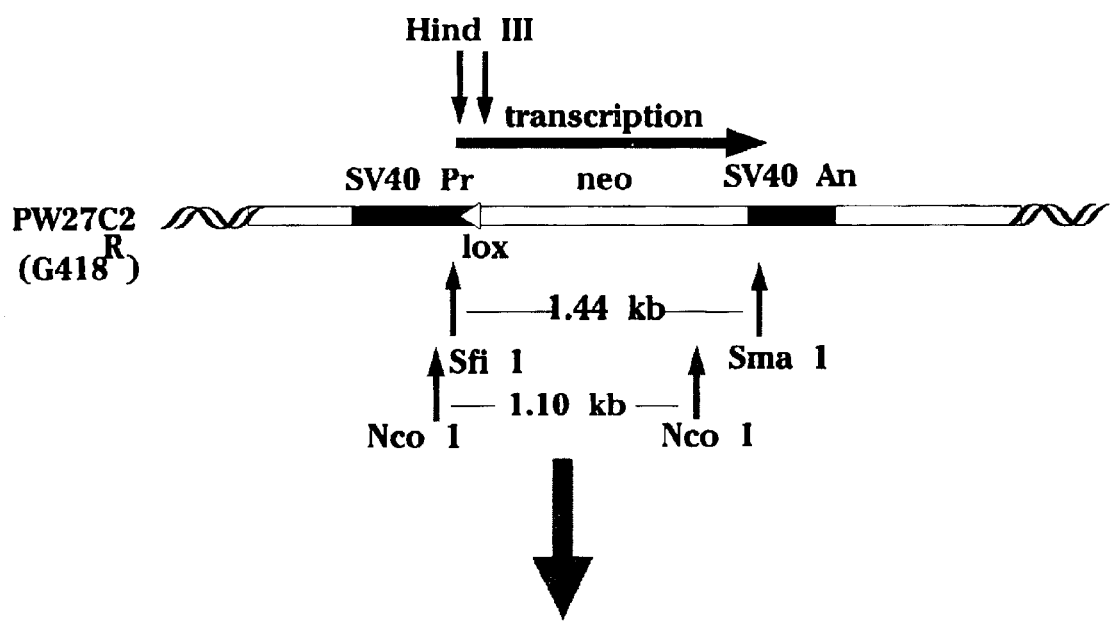
FIG. 6A is a diagrammatic representation of the structure of a DNA insertion in a human cell line, PW27C2, comprising a single loxP site between a promoter and a drug resistance gene (neo).
Figure 6B:
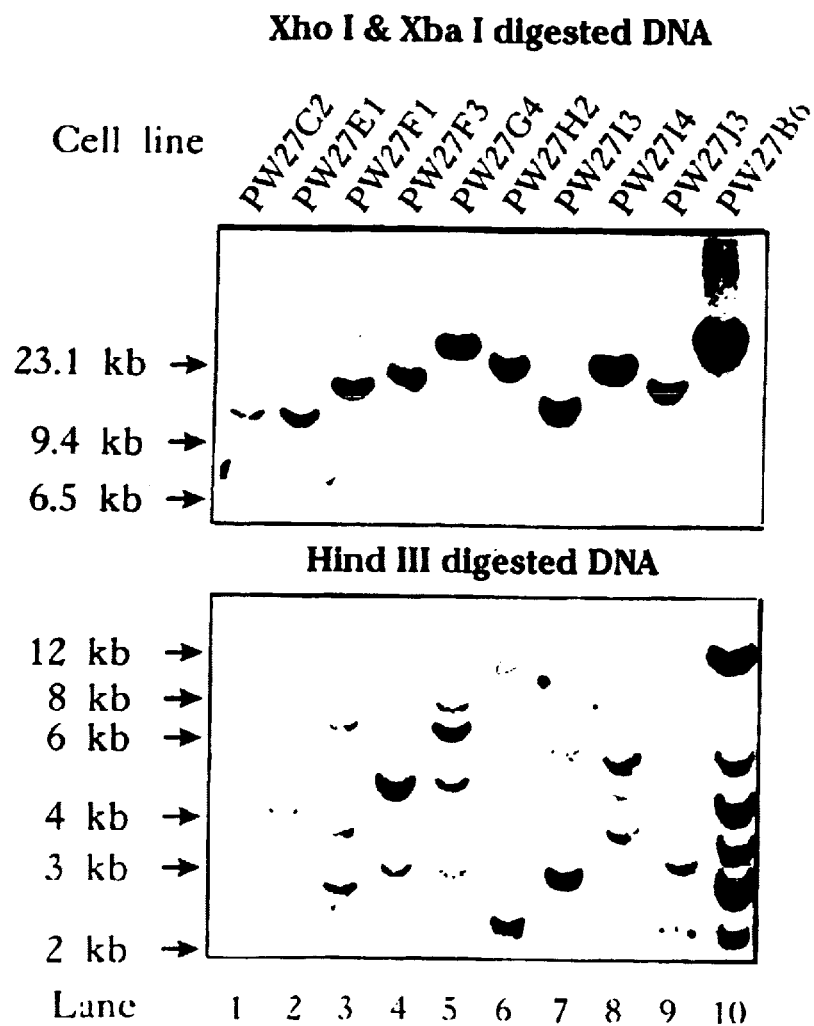
FIG. 6B is a Southern blot hybridization analysis of selected transformed cell lines transformed by plasmid pBS74.

It was important to determine whether Cre enzyme expressed in AdCre infected cells could also act on loxP sites present in the chromosomal DNA of the host cell. Therefore, we constructed a series of human cell lines transformed by the plasmid pBS74 (obtained from Brian Sauer) which contains a single loxP site between the SV40 promoter and the coding sequences for the neo gene (expression of neo in mammalian cells results in resistance to G418) (FIG. 6A). (In this and subsequent illustrations, wavy double lines are meant to represent cellular DNA flanking the plasmid DNA insert. Other features of the inserted DNA sequences are indicated in the illustrations.) Several HT1080 derived cell lines transformed by pBS74 and resistant to G418 were established and a few were analyzed by Southern hybridization. The precise structure of integrated pBS74 sequences was not determined, but those skilled in the art will appreciate that cell line PW27B6 appeared to have multiple copies of pBS74 DNA and therefore many loxP sites, whereas lines PW27C2 and PW27E1 appeared to have a single insertion of pBS74 sequences and therefore a single copy of loxP.

Figure 6C:
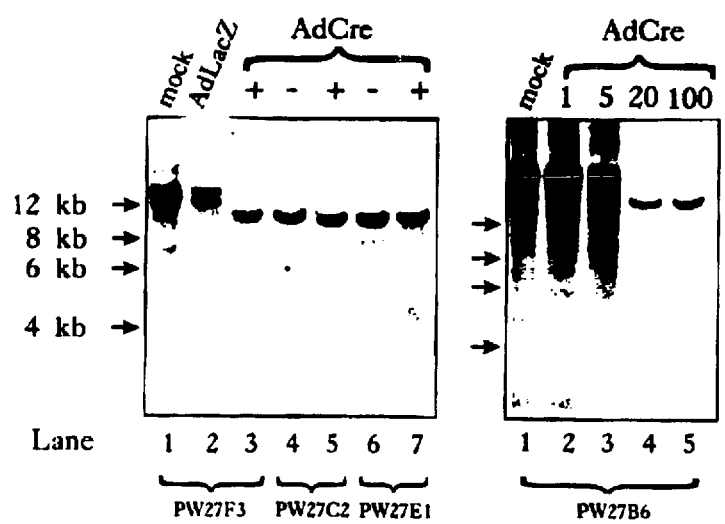
FIG. 6C is a Southern blot hybridization analysis of DNA from cell lines: PW27F3, PW27C2, PW27E1 and PW27B6, after AdCre infection, showing rearrangement of DNA in PW27F3 and PW27B6 cells but not in PW27C2 and PW27E1 cells.

Having obtained cell lines that had many loxP sites (line PW27B6), or a single loxP site (lines PW27C2 and PW27E1) integrated into their chromosomal DNA, it was possible to examine the effect of infection with AdCre on chromosomal DNA structure in the vicinity of the integrated pBS74 sequences containing loxP. Thus, cell lines PW27B6 and PW27C2 were infected with AdCre at various multiplicities of infection (PFU/cell) and 3 days after infection cell DNA was extracted, purified, and analyzed by Southern blot hybridization using radioactive pBS74 DNA as a probe (FIG. 6C). Those skilled in the art will appreciate that infection with AdCre induced significant DNA rearrangements in the cell line, PW27B6, that had multiple loxP sites. Thus Cre expressed from AdCre was capable of inducing recombination between two or more loxP sites situated in chromosomal DNA sites of a human cell. Those skilled in the art will appreciate that similar results would be obtained in other mammalian cells that could be infected with AdCre and that contained loxP sites integrated into their chromosomal DNA. It is important to note that the DNA structure of cell lines PW27C2 and PW27E 1 that contain single insertions of loxP was unaltered by infection with AdCre. Thus Cre did not induce rearrangement of DNA sequences in the genome of cells containing a single loxP site.

EXAMPLE 7

Figure 7A:
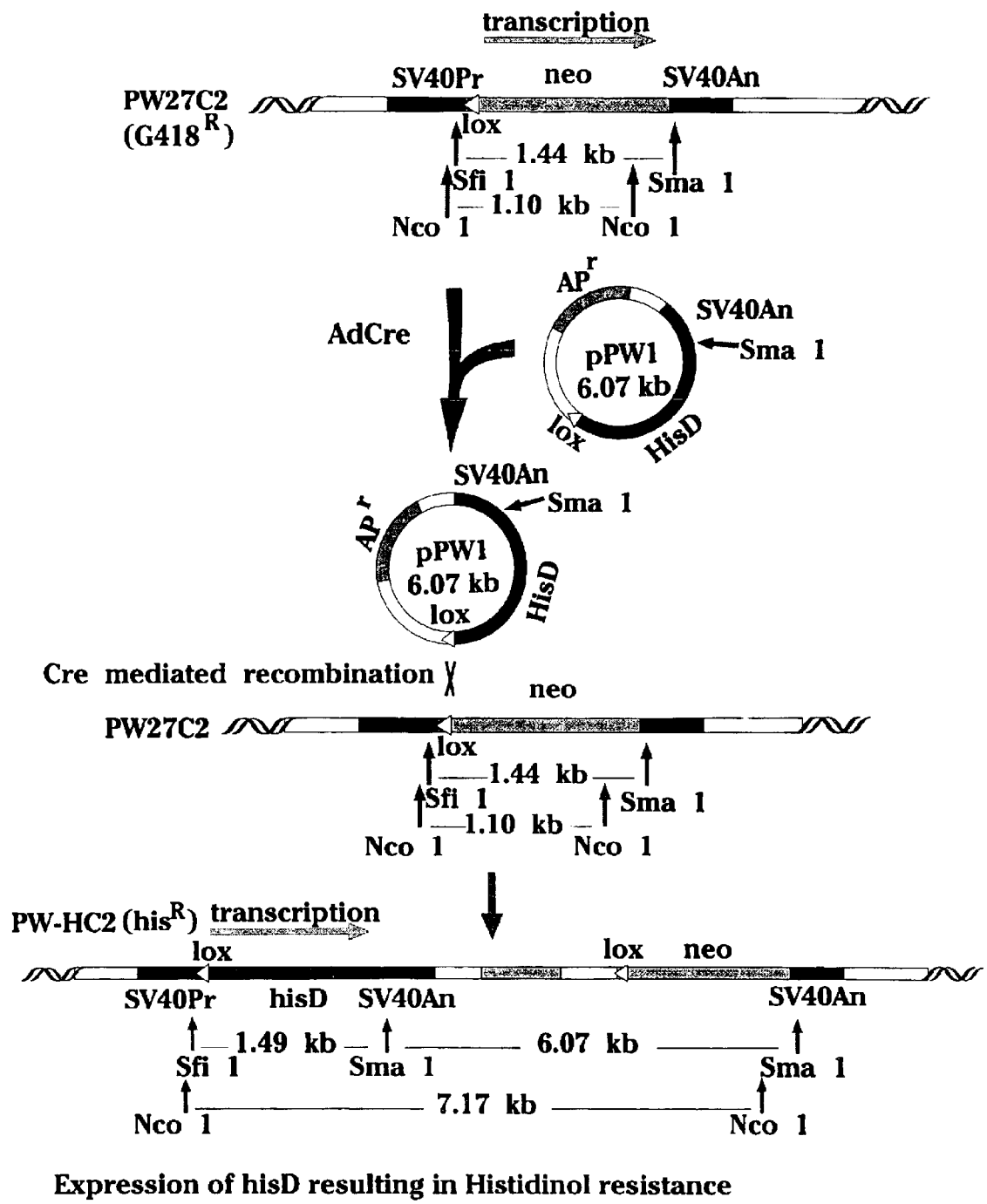
FIG. 7A is a diagrammatic representation of the structure that results from Cre recombinase mediated insertion of a plasmid containing a loxP site adjacent to a promoterless drug resistance marker, HisD, into the loxP site engineered downstream of a promoter in cell line, PW27C2.

Having demonstrated that a cell line such as PW27B6 with multiple loxP sites could be infected with AdCre resulting in expression of Cre recombinase and induction of recombination between loxP sites, it was important to be able to determine whether AdCre could be used to switch gene expression on or off in appropriately designed and engineered cells. To this end we constructed cell lines by the method illustrated in FIG. 7A. Cell line PW27C2, containing a single loxP site, was infected with AdCre and incubated for 24 hrs to allow expression of Cre. The cell were then transfected with plasmid pPW1 that was engineered to contain a single loxP site near the start of a promoterless HisD coding sequence. Cre mediated recombination resulted in insertion of pPW1 sequences into the loxP site located chromosomally in the genome of PW27C2 cells, generating a number of histidinol resistant cell lines, among them the cell line PW-HC2 with an arrangement of DNA segments in the order: SV40 promoter, loxP site, coding sequences for His D, SV40 polyadenylation signal, plasmid DNA, loxP site, neo coding sequences, and finally SV40 polyadenylation signal as diagramed at the bottom of FIG. 7A. The cell line PW-HC2 was resistant to histidinol and sensitive to G418 because in the structure as diagramed, the HisD gene is immediately downstream of the SV40 promoter whereas neo is not adjacent to a promoter and therefore is not expressed.

Figure 7B:
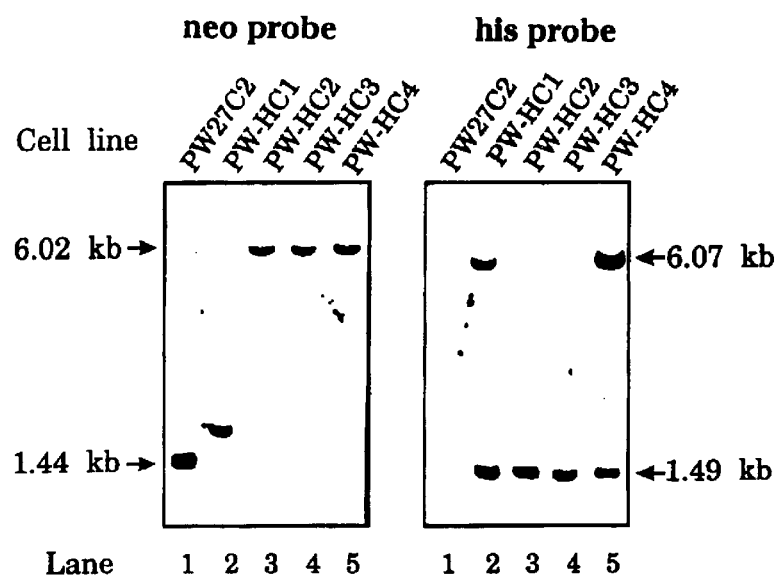
FIG. 7B is a Southern blot hybridization analysis of DNA extracted from cell lines PW-HC1, PW-HC2, PW-HC3, and PWHC4, providing evidence for Cre mediated insertion of pPW1 plasmid DNA into the loxP site of the parental cell line PW27C2.

Southern blot hybridization analysis (FIG. 7B) was carried out on Sfi I and Sma I digested DNA extracted from cell line PW-HC2 and 3 additional cell lines, PW-HC1, PW-HC3, and PW-HC4, in comparison to the parental line PW27C2. This analysis confirmed that the structure of integrated plasmid DNA sequences in PW-HC2 and PW-HC3 was as diagramed in FIG. 7A. Thus a person skilled in the art will appreciate that Sfi I and Sma I digested DNA from both PW-HC2 and PW-HC3 cell lines resulted in Southern blot hybridization patterns that showed the predicted radio labeled bands at 6.07 kb or 1.49 kb when the blots were probed with sequences hybridizing to neo, or his sequences, respectively. Two other cell lines PW-HC1 and PW-HC4 gave patterns on Southern blots that suggested other, more complicated integration patterns, that probably resulted from insertion of more than one copy of pPW1 DNA.

EXAMPLE 8

Figure 8A:
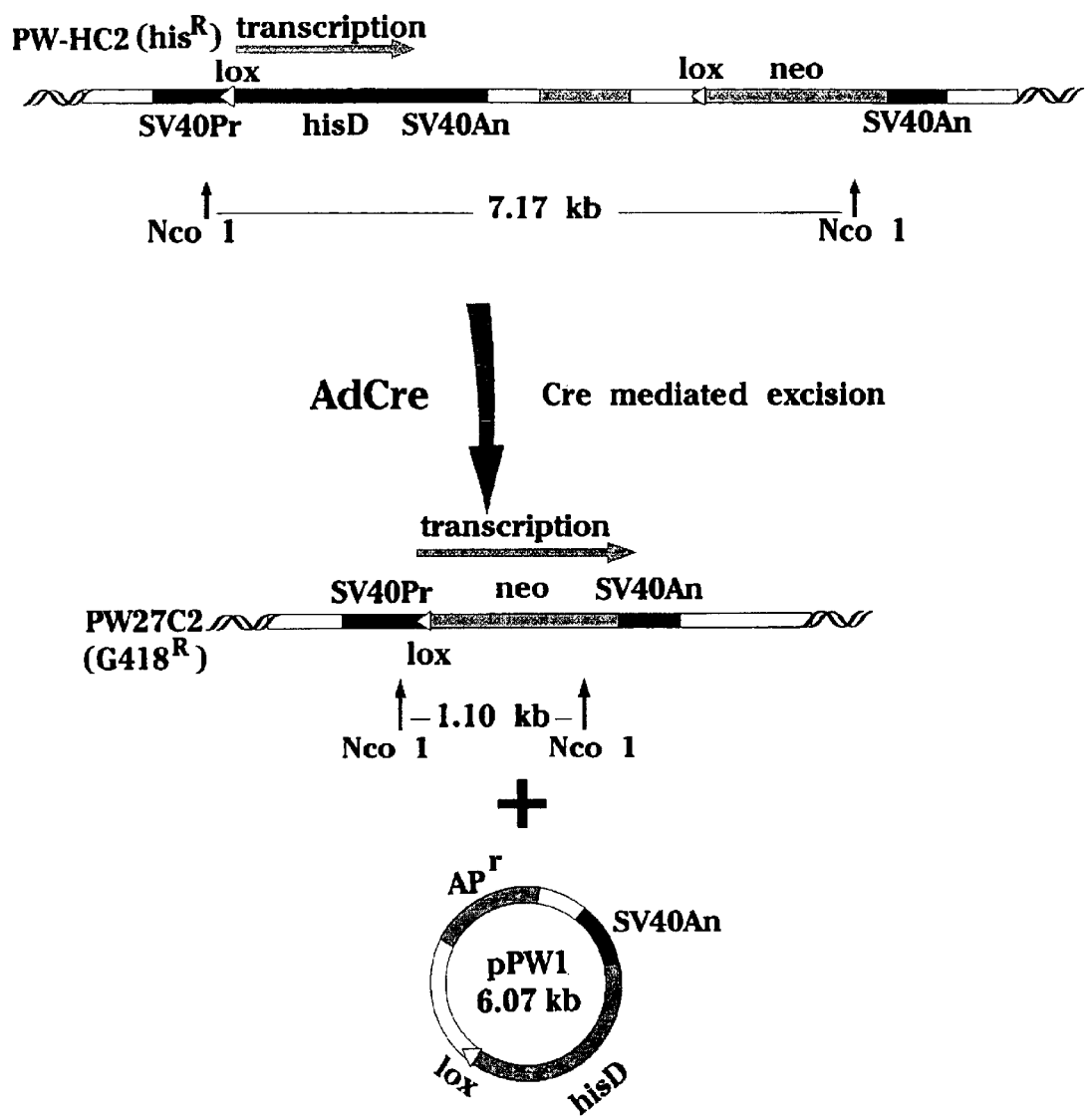
FIG. 8A is a diagrammatic representation of the structures that result from Cre recombinase mediated excision of the drug resistance gene, HisD, and adjacent sequences flanked by loxP sites, resulting in conversion of a cell line from histidinol resistance to G418 resistance.

Having demonstrated that Cre produced following AdCre infection could catalyze site specific integration of a subsequently transfected plasmid such as pPW1 into a loxP site in chromosomal DNA, it was important to demonstrate that the reverse reaction could also be induced by Cre following infection of PW-HC2 cells with AdCre as diagramed in FIG. 8A. Thus histidinol resistant PW-HC2 cells were infected with AdCre and 3 days post infection were reseeded at low cell density in non selective medium to obtain colonies derived from single cells. Isolated colonies were then reseeded into culture dishes containing medium with G418, or histidinol, or no selection, and resistance to G418 or histidinol was determined by cell growth in selective medium.

Figure 8B:
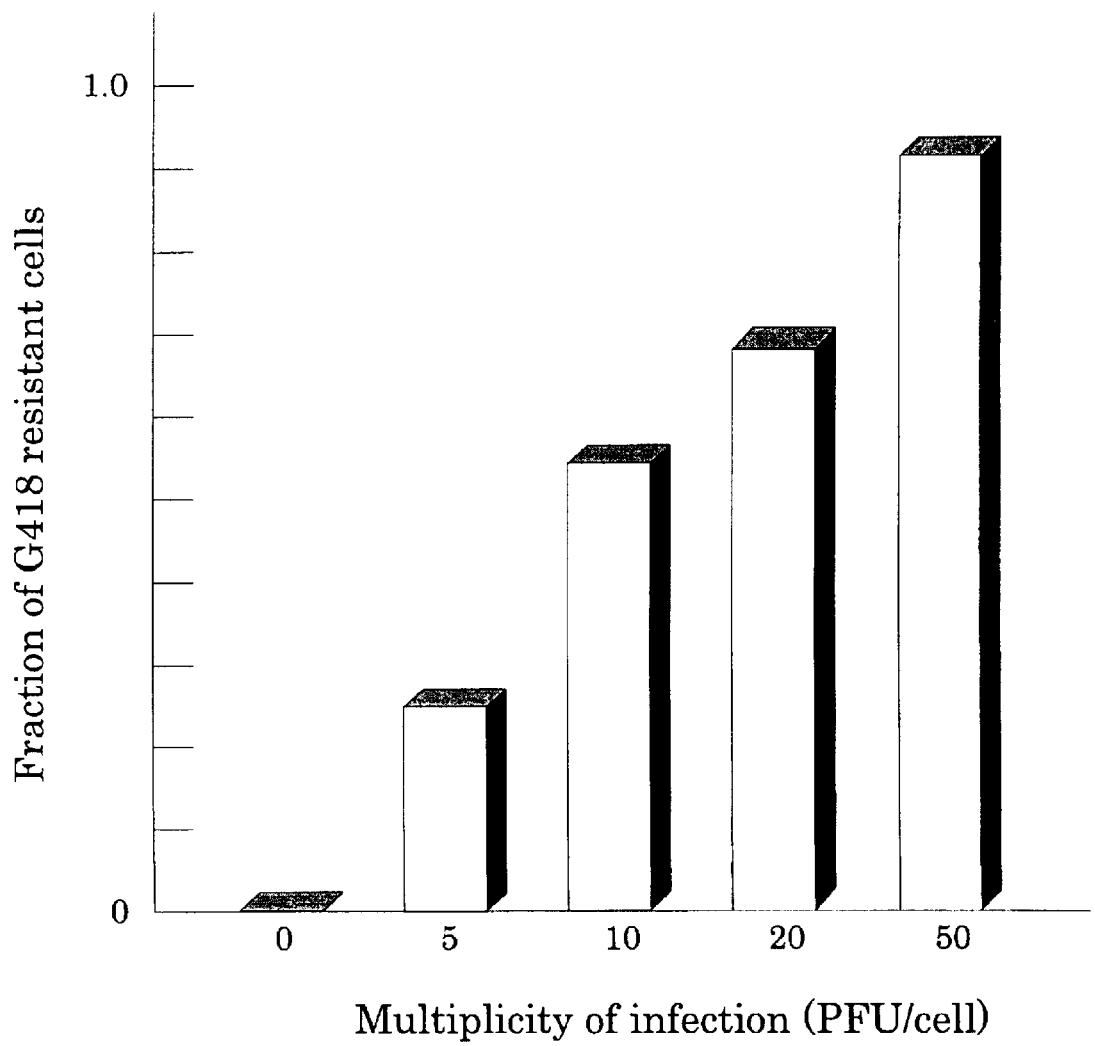
FIG. 8B presents quantitative evidence for ability of Cre synthesized in cells infected by AdCre to catalyze excision of a DNA segment flanked by loxP sites and to switch on expression of one gene, neo encoding G418 resistance, while switching off expression of another gene, HisD encoding histidinol resistance.

As can be seen from the results in FIG. 8B, infection of PW-HC2 cells with AdCre caused very efficient conversion of histidinol resistance to G418 resistance, resulting in over 90% of the infected cells becoming G418 resistant following infection at 50 PFU/cell. In every case, cells that became resistant to G418 simultaneously lost the ability to grow in histidinol, a result which is consistent with the excision of pPW1 as diagramed in FIG. 8A. Thus AdCre infection and expression of Cre recombinase could switch on expression of the neo gene and switch off expression of HisD.

It will be appreciated by those skilled in the art that other cell types that can be infected with adenoviruses could also be infected with AdCre to produce Cre recombinase. It will be appreciated that if such cells have multiple loxP sites in their chromosomal DNA, Cre expression in such cells will equally result in recombination, excision or rearrangement of sequences flanked by loxP sites. It will be appreciated that such recombination, excision or rearrangement, will have the capability of regulating expression of appropriately engineered genes in the vicinity of loxP sites, resulting in switch on of gene expression or switch off, depending on the design and construction of the integrated sequences. For example if a gene is constructed such that it is adjacent to a promoter that is oriented such that transcription from the promoter is directed away from said gene, then expression of the gene will not occur. If said promoter is flanked by loxP sites that are oriented in opposite orientation with respect to one another, then Cre recombinase provided by AdCre infection will result in inversion of sequences flanked by the oppositely oriented loxP sites, causing the promoter to be directed toward the coding sequences for the adjacent gene in a fraction of infected cells, and thereby causing expression of said gene.

On the other hand, it will be appreciated that if a promoter is oriented such that transcription is directed toward and through an adjacent gene and the gene is expressed, and if the promoter is flanked by loxP sites in parallel orientation with respect to one another, then expression of Cre recombinase provided by infection with AdCre will result in excision of the promoter element, causing transcription to cease in the infected cells and thereby switching off expression of said gene. It will be appreciated by those skilled in the art that if a gene construct be engineered such that a promoter and downstream sequences are interrupted by a DNA segment (e.g. a "spacer" as in example 5) that is flanked by loxP sites in parallel orientation and that prevents gene expression unless said spacer is excised, then provision of Cre recombinase by AdCre infection of cells containing said gene construct will result in excision of said spacer and expression of the gene.

It will equally be appreciated that an entire gene may be flanked by loxP sites and introduced into the chromosomal DNA of a mammalian cell and may be designed and constructed such that said gene is expressed in said cells. If said cells are subsequently infected with AdCre it will be appreciated that excision of said gene will result in loss of the gene from the chromosomes of said infected cells and loss of expression of said gene. These examples are not meant to be limiting. Those skilled in the art will appreciate that a variety of DNA constructs could be designed and introduced into cells such that said constructs would respond to Cre provided by AdCre infection to result in rearrangement of DNA and alteration in gene expression.

EXAMPLE 9

The above described results demonstrate that adenovirus-based vector embodiments of this invention efficiently deliver genes encoding a recombinase such as the Cre recombinase to target cells. The resulting expression of Cre protein induces rearrangement of DNA sequences flanked by loxP sites that are the target sites for recombination catalyzed by the Cre enzyme. The observed DNA rearrangements result in expression of an appropriately designed and constructed coding sequence such as an adjacent luciferase cDNA. The above described experimental methods are not intended to be limiting. The present invention encompasses a similar result with genes encoding other recombinases or DNA modifying enzymes. These genes can be readily introduced into Ad vectors and used to introduce said recombinases or DNA modifying enzymes to cause rearrangements of appropriately designed and engineered DNA sequences.

In addition the invention contemplates the use of such vectors to introduce Cre, or other recombinases or DNA modifying enzymes into any mammalian cells that can be infected with said vectors or into tissues or organs of animals whose cells can be infected by said vectors. For example, the liver may be infected with a vector expressing Cre by infusing the liver via the portal vein with the vector, or lung tissues may be infected by intratracheal administration of vectors, or skin may be infected by intradermal inoculation of vectors, or by abrasion and treatment with virus suspensions.

It will be readily apparent to a person skilled in the art that other combinations of loxP sites, genes and coding sequences can be designed such that expression of such genes can be regulated by the action of Cre recombinase. Thus DNA segments can be engineered that have loxP sites in other positions and orientations within or in the vicinity of a gene such that expression of such gene may be turned on or off through the action of Cre recombinase. For example, a person skilled in the art may design and construct a gene that contains loxP sequences at sites flanking and including the coding sequences for a protein, but excluding a promoter, such that excision of the coding sequences caused by Cre will result in excision of said coding sequences and consequent cessation of protein synthesis.

It will also be readily apparent to a person skilled in the art that such DNA constructions can be introduced into the genomes of mammalian cells or into the genome of transgenic animals by standard techniques so that the resulting mammalian cells or transgenic animals will respond to administration of a vector expressing Cre or similar recombinase or DNA modifying enzyme resulting in regulation of gene expression in said cells or said transgenic animal. The invention contemplates the use of Ad vectors expressing Cre or similar recombinase or DNA modifying enzyme and cells or transgenic animals containing appropriately designed and constructed DNA sequences to regulate gene expression for production of proteins.

Figure 9:
FIG. 9 is a diagrammatic representation of the means by which an Ad vector such as AdCre could be used to regulate gene expression in a transgenic animal that contains a transgene regulated by a molecular switch that is responsive to Cre mediated recombination.
Figure 9:
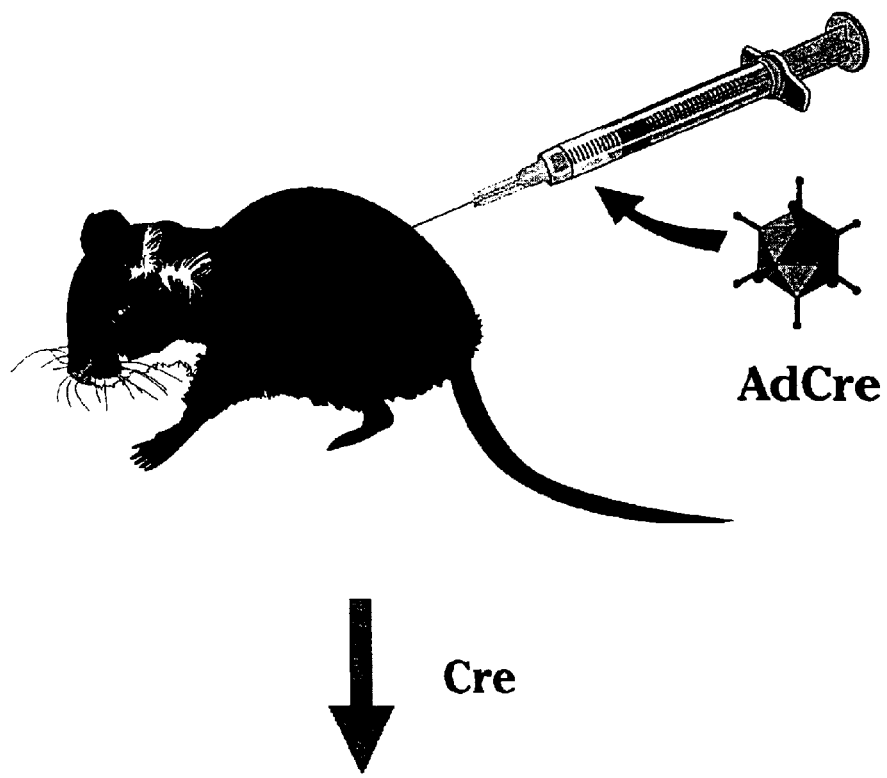

It will be appreciated by those skilled in the art that the use of recombinases expressed by Ad vectors is not limited to mammalian cells in culture. A person skilled in the art can readily develop transgenic animals that contain in their DNA, constructs similar to those described in the preceding examples. For example a person skilled in the art can readily derive a transgenic mouse into whose DNA has been introduced a construct having the structure illustrated in FIG. 9, whereby a DNA sequence such as that encoding bacterial .beta.-galactosidase is placed downstream of a promoter but separated from the promoter by a "spacer" DNA flanked by loxP sites, as illustrated, such that expression of .beta.-galactosidase is prevented unless said spacer is excised. It will be appreciated that infection of said animals by injection or inoculation with an Ad vector expressing Cre will result in expression of Cre recombinase in the tissues of said animals and induction of Cre specific recombination in said transgenic animals. Cre mediated excision of said spacer DNA as demonstrated in examples 5 and 8 will result in expression of .beta.-galactosidase in tissues in which Cre is expressed as a result of AdCre infection and juxtaposition of the promoter with the .beta.-galactosidase coding sequences.

To summarize: in this example, expression of .beta.-galactosidase (LacZ) in the transgenic animal is prevented because the spacer segment separates the coding sequences for beta.-galactosidase from the promoter.

Injection of an adenovirus vector expressing Cre results in production of Cre enzyme in cells infected by the vector, and Cre mediated recombination of the target loxP sequences causes excision of the spacer segment and results in expression of .beta.-galactosidase. This example is not meant to be limiting. A person skilled in the art will readily appreciate that the LacZ gene in this example can be substituted with coding sequences for any other enzyme or regulatory protein such as the retinoblastoma (Rb) gene product, the p53 gene product, neu or such proteins whose expression might be desirable.

A person skilled in the art will also readily appreciate that regulation of gene expression can encompass both a switch on of expression and/or a switch off as in example 8 in which expression of neo (G418 resistance) is switched on and HisD (histidinol resistance) is turned off by the action of Cre expressed in PW-HC2 cells infected by AdCre.

The Ad vector expressing Cre could be introduced into any of a variety of tissues, such as skin, liver, muscle, lung etc of live animals to induce expression of the regulated transgene in cells of those tissues. The transgenic animals that could be infected by an Ad vector in this way are not limited to mice. A person skilled in the art will readily appreciate that the AdCre vector or similar vector could also be used to treat transgenic goats, sheep, or cows or other species into which suitable transgenes can be introduced, to regulate expression of appropriately designed transgenes. The examples of protein expression regulated by Cre expression are not meant to be limiting. A person skilled in the art will readily appreciate that DNA rearrangements induced by Cre, or by other recombinases, or by other DNA modifying enzymes that can be introduced into cells by infection with an appropriately designed vector, can be used to regulate expression of RNAs that do not encode proteins, or can be used to alter DNA structure in such ways as might affect binding of regulatory proteins that control gene expression or DNA replication.

What is claimed is:

1. An adenovirus comprising an inserted expression cassette comprising a promoter sequence, a coding sequence of a gene, and a transcription termination site, and site-specific recombinase target sites positioned to remove or invert a portion of the expression cassette, whereby recombination between said target sites mediated by a site-specific recombinase alters expression of the coding sequence of the gene.

2. An adenovirus comprising an inserted expression cassette comprising a promoter sequence, a coding sequence of a gene, and a transcription termination site, and site-specific recombinase target sites flanking the promoter sequence of said expression cassette that promotes expression of the gene, whereby recombination between said target sites mediated by a site-specific recombinase removes the promoter sequence, resulting in decreased expression of the coding sequence of the gene.

3. The adenovirus of claim 2, wherein the coding sequence of the gene is from a non-adenoviral source.

4. An adenovirus comprising an inserted expression cassette comprising a promoter sequence, a coding sequence of a gene, and a transcription termination site, the promoter sequence directed away from said gene, and two site-specific recombinase target sites flanking said promoter sequence but oriented in opposite orientation to one another, whereby recombination between said target sites mediated by a site-specific recombinase inverts the promoter sequence, resulting in increased expression of the coding sequence of the gene.

5. The adenovirus of claim 4, wherein the coding sequence of the gene is from a non-adenoviral source.

6. An adenovirus comprising an inserted expression cassette comprising a promoter sequence, a coding sequence of a gene, a DNA spacer sequence located between the promoter sequence and the coding sequence, and a transcription termination site, and site-specific recombinase target sites flanking the DNA spacer sequence, whereby recombination between said target sites mediated by a site-specific recombinase removes the DNA spacer sequence, resulting in increased expression of the coding sequence of the gene.

7. The adenovirus of claim 6, wherein the coding sequence of the gene is from a non-adenoviral source.

8. An adenovirus comprising an inserted expression cassette comprising a promoter sequence, a coding sequence of a gene, and a transcription termination site, and site-specific recombinase target sites flanking the coding sequence of the gene, whereby recombination between said target sites mediated by a site-specific recombinase removes the coding sequence, resulting in decreased of the coding sequence of the gene.

9. The adenovirus of claim 8, wherein the coding sequence of the gene is from a non-adenoviral source.

10. An adenovirus comprising an inserted expression cassette comprising a promoter sequence, a coding sequence of a gene, and a transcription termination site, a portion of said expression cassette comprising the coding sequence oriented in an opposite direction to normal translation of the coding sequence of the gene, and two site-specific recombinase target sites flanking said coding sequence but oriented in opposite orientation to one another, whereby recombination between said target sites mediated by a site-specific recombinase inverts the coding sequence, resulting in increased expression of the coding sequence of the gene.

11. The adenovirus of claim 10, wherein the coding sequence of the gene is from a non-adenoviral source.

12. An adenovirus comprising a promoter sequence, a coding sequence of a gene, a transcription termination site, and site-specific recombinase target sites flanking the coding sequence of the gene, whereby recombination between said target sites mediated by a site-specific recombinase removes the coding sequence of the gene, resulting in decreased expression of the gene.

13. The adenovirus of claim 12, wherein the coding sequence of the gene is from a non-adenoviral source.

14. An adenovirus comprising a promoter sequence, a coding sequence of a gene, and a transcription termination site, said coding sequence of the gene oriented in an opposite direction to normal translation of the gene, and two site-specific recombinase target sites flanking said coding sequence of the gene but oriented in opposite orientation to one another, whereby recombination between said target sites mediated by a site-specific recombinase inverts the gene, resulting in increased expression of the coding sequence of the gene.

15. The adenovirus of claim 14, wherein the coding sequence of the gene is from a non-adenoviral source.

* * * * *